United States Patent
Refai et al.

(10) Patent No.: US 8,702,719 B2
(45) Date of Patent: *Apr. 22, 2014

(54) SURGICAL INSTRUMENT AND METHOD OF USE FOR INSERTING AN IMPLANT BETWEEN TWO BONES

(75) Inventors: Daniel Refai, Saint Louis, MO (US); Jeffrey T. Ebersole, Columbia City, IN (US); Jeffrey A. Farris, Berne, IN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/312,486

(22) Filed: Dec. 6, 2011

(65) Prior Publication Data

US 2012/0310293 A1  Dec. 6, 2012

Related U.S. Application Data

(63) Continuation of application No. 12/252,552, filed on Oct. 16, 2008, now Pat. No. 8,142,441.

(51) Int. Cl.
*A61B 17/58* (2006.01)
*A61B 17/60* (2006.01)

(52) U.S. Cl.
USPC .................................................. 606/99

(58) Field of Classification Search
USPC ............ 623/17.11–17.16; 606/63, 99, 60, 606/246–249, 279
See application file for complete search history.

(56) References Cited

U.S. PATENT DOCUMENTS 2,333,033 A * 10/1943 Mraz ............................. 606/57
4,157,715 A * 6/1979 Westerhoff ................... 606/60
4,289,123 A * 9/1981 Dunn ............................ 606/250
4,386,603 A * 6/1983 Mayfield ...................... 606/105
4,401,112 A * 8/1983 Rezaian ........................ 606/279
4,553,273 A * 11/1985 Wu ............................... 623/23.45

(Continued)

FOREIGN PATENT DOCUMENTS

DE  30 23 942  1/1982
DE  37 29 600  3/1989

(Continued)

OTHER PUBLICATIONS

U.S. Appl. No. 12/252,552, Notice of Allowance mailed Dec. 13, 2011, 12 pgs.

(Continued)

*Primary Examiner* — Alvin Stewart
(74) *Attorney, Agent, or Firm* — RatnerPrestia

(57) ABSTRACT

The surgical instrument includes a handle assembly and an elongate body that has first and second ends with the first end being located adjacent to the handle assembly and the second end being moveably connected to an implant engagement assembly. The surgical instrument also has a length control mechanism that includes a gripping portion, a drive shaft and a gear assembly. The surgical instrument further has a locking mechanism that includes a gripping portion, a connecting rod and a coupling end. The length control mechanism functions to adjust the overall length of an implant that is held by the implant engagement assembly before being implanted in vivo. The locking mechanism operates to secure the overall length of the implant following final length adjustment and implantation. A surgical method for using the surgical instrument, a method of fabrication and a spinal implant insertion kit is also disclosed.

16 Claims, 11 Drawing Sheets

(56) References Cited

U.S. PATENT DOCUMENTS

| | | | | |
|---|---|---|---|---|
| 4,554,914 A * | 11/1985 | Kapp et al. | 606/86 A |
| 4,599,086 A * | 7/1986 | Doty | 606/86 A |
| 4,636,217 A * | 1/1987 | Ogilvie et al. | 623/17.11 |
| 4,657,550 A * | 4/1987 | Daher | 623/17.11 |
| 4,762,031 A * | 8/1988 | Bradley | 81/57.22 |
| 4,877,020 A * | 10/1989 | Vich | 606/86 R |
| 4,892,546 A * | 1/1990 | Kotz et al. | 623/23.45 |
| 4,932,975 A * | 6/1990 | Main et al. | 623/17.12 |
| 4,997,432 A * | 3/1991 | Keller | 623/17.11 |
| 5,002,576 A * | 3/1991 | Fuhrmann et al. | 623/17.15 |
| 5,122,130 A * | 6/1992 | Keller | 606/86 A |
| 5,236,460 A * | 8/1993 | Barber | 623/17.15 |
| 5,246,458 A * | 9/1993 | Graham | 623/17.14 |
| 5,281,226 A * | 1/1994 | Davydov et al. | 623/16.11 |
| 5,290,312 A * | 3/1994 | Kojimoto et al. | 623/17.15 |
| 5,336,223 A * | 8/1994 | Rogers | 606/258 |
| 5,344,459 A * | 9/1994 | Swartz | 623/14.12 |
| 5,405,391 A * | 4/1995 | Hednerson et al. | 623/17.15 |
| 5,413,602 A * | 5/1995 | Metz-Stavenhagen | 623/17.15 |
| 5,443,514 A * | 8/1995 | Steffee | 128/898 |
| 5,458,641 A * | 10/1995 | Ramirez Jimenez | 623/17.11 |
| 5,480,442 A * | 1/1996 | Bertagnoli | 623/17.14 |
| 5,571,190 A | 11/1996 | Ulrich | |
| 5,571,192 A * | 11/1996 | Schonhoffer | 623/17.11 |
| 5,599,279 A * | 2/1997 | Slotman et al. | 600/201 |
| 5,658,335 A * | 8/1997 | Allen | 623/17.16 |
| 5,702,453 A * | 12/1997 | Rabbe et al. | 623/17.16 |
| 5,702,455 A * | 12/1997 | Saggar | 623/17.15 |
| 5,716,415 A * | 2/1998 | Steffee | 623/17.16 |
| 5,723,013 A * | 3/1998 | Jeanson et al. | 623/17.16 |
| 5,732,992 A * | 3/1998 | Mauldin | 294/119.1 |
| 5,776,197 A * | 7/1998 | Rabbe et al. | 623/17.15 |
| 5,776,198 A * | 7/1998 | Rabbe et al. | 623/17.15 |
| 5,782,830 A * | 7/1998 | Farris | 606/99 |
| 5,800,547 A * | 9/1998 | Schafer et al. | 623/17.16 |
| 5,888,223 A * | 3/1999 | Bray, Jr. | 623/17.16 |
| 5,916,267 A * | 6/1999 | Tienboon | 623/17.11 |
| 5,989,290 A * | 11/1999 | Biedermann et al. | 623/17.11 |
| 6,015,436 A * | 1/2000 | Schonhoffer | 623/17.16 |
| 6,042,582 A * | 3/2000 | Ray | 606/86 A |
| 6,045,579 A * | 4/2000 | Hochshuler et al. | 623/17.16 |
| 6,066,174 A * | 5/2000 | Farris | 606/206 |
| 6,080,193 A * | 6/2000 | Hochshuler et al. | 623/17.16 |
| 6,106,557 A | 8/2000 | Robioneck | |
| 6,113,602 A * | 9/2000 | Sand | 606/86 A |
| 6,113,605 A * | 9/2000 | Storer | 606/99 |
| 6,126,660 A * | 10/2000 | Dietz | 606/90 |
| 6,126,674 A * | 10/2000 | Janzen | 606/206 |
| 6,129,763 A * | 10/2000 | Chauvin et al. | 623/17.11 |
| 6,159,215 A * | 12/2000 | Urbahns et al. | 606/86 R |
| 6,176,881 B1 * | 1/2001 | Schar et al. | 623/17.11 |
| 6,190,413 B1 * | 2/2001 | Sutcliffe | 623/17.11 |
| 6,190,414 B1 * | 2/2001 | Young et al. | 623/17.15 |
| 6,193,755 B1 * | 2/2001 | Metz-Stavenhagen et al. | 623/17.11 |
| 6,193,756 B1 * | 2/2001 | Studer et al. | 623/17.15 |
| 6,200,348 B1 * | 3/2001 | Biedermann et al. | 623/17.11 |
| 6,214,050 B1 * | 4/2001 | Huene | 623/17.15 |
| 6,261,296 B1 * | 7/2001 | Aebi et al. | 606/99 |
| 6,267,763 B1 * | 7/2001 | Castro | 606/86 A |
| 6,296,665 B1 * | 10/2001 | Strnad et al. | 623/17.16 |
| 6,299,644 B1 * | 10/2001 | Vanderschot | 623/17.15 |
| 6,319,257 B1 * | 11/2001 | Carignan et al. | 606/99 |
| 6,344,057 B1 * | 2/2002 | Rabbe et al. | 623/17.11 |
| 6,352,556 B1 * | 3/2002 | Kretschmer et al. | 623/17.11 |
| 6,375,682 B1 * | 4/2002 | Fleischmann et al. | 623/17.12 |
| 6,375,683 B1 * | 4/2002 | Crozet et al. | 623/17.15 |
| 6,395,032 B1 * | 5/2002 | Gauchet | 623/17.12 |
| 6,395,034 B1 * | 5/2002 | Suddaby | 623/17.15 |
| 6,436,119 B1 * | 8/2002 | Erb et al. | 606/198 |
| 6,454,806 B1 * | 9/2002 | Cohen et al. | 623/17.15 |
| 6,478,800 B1 * | 11/2002 | Fraser et al. | 606/99 |
| 6,524,341 B2 * | 2/2003 | Lang et al. | 623/17.15 |
| 6,562,074 B2 * | 5/2003 | Gerbec et al. | 623/17.15 |
| 6,616,695 B1 * | 9/2003 | Crozet et al. | 623/17.11 |
| 6,648,917 B2 * | 11/2003 | Gerbec et al. | 623/17.11 |
| 6,652,533 B2 * | 11/2003 | O'Neil | 606/100 |
| 6,660,038 B2 * | 12/2003 | Boyer et al. | 623/17.15 |
| 6,699,246 B2 * | 3/2004 | Zucherman et al. | 606/249 |
| 6,712,825 B2 * | 3/2004 | Aebi et al. | 606/90 |
| 6,716,218 B2 * | 4/2004 | Holmes et al. | 606/105 |
| 6,719,796 B2 * | 4/2004 | Cohen et al. | 623/17.15 |
| 6,723,126 B1 * | 4/2004 | Berry | 623/17.11 |
| 6,730,088 B2 * | 5/2004 | Yeh | 606/247 |
| 6,746,454 B2 * | 6/2004 | Winterbottom et al. | 606/99 |
| 6,752,832 B2 * | 6/2004 | Neumann | 623/17.15 |
| 6,755,841 B2 * | 6/2004 | Fraser et al. | 606/99 |
| 6,783,547 B2 * | 8/2004 | Castro | 623/17.16 |
| 6,808,538 B2 * | 10/2004 | Paponneau | 623/17.16 |
| 6,814,737 B2 * | 11/2004 | Cauthen | 606/99 |
| 6,821,298 B1 * | 11/2004 | Jackson | 623/17.15 |
| 6,835,206 B2 * | 12/2004 | Jackson | 623/17.11 |
| 6,835,207 B2 * | 12/2004 | Zacouto et al. | 623/17.12 |
| 6,852,129 B2 * | 2/2005 | Gerbec et al. | 623/17.15 |
| 6,863,673 B2 * | 3/2005 | Gerbec et al. | 606/99 |
| 6,866,682 B1 * | 3/2005 | An et al. | 623/17.15 |
| 6,902,579 B2 * | 6/2005 | Harms et al. | 623/17.11 |
| 6,908,485 B2 * | 6/2005 | Crozet et al. | 623/17.16 |
| 6,953,477 B2 * | 10/2005 | Berry | 623/17.11 |
| 6,981,989 B1 * | 1/2006 | Fleischmann et al. | 623/17.11 |
| 7,022,138 B2 * | 4/2006 | Mashburn | 623/17.13 |
| 7,029,498 B2 * | 4/2006 | Boehm et al. | 623/17.11 |
| 7,056,343 B2 * | 6/2006 | Schafer et al. | 623/17.11 |
| 7,070,598 B2 * | 7/2006 | Lim et al. | 606/99 |
| 7,081,118 B2 * | 7/2006 | Weber et al. | 606/90 |
| 7,090,679 B2 * | 8/2006 | Saint-Martin et al. | 606/99 |
| 7,118,580 B1 * | 10/2006 | Beyersdorff et al. | 606/99 |
| 7,156,874 B2 * | 1/2007 | Paponneau et al. | 623/17.11 |
| 7,169,153 B2 * | 1/2007 | Keller | 606/99 |
| 7,169,182 B2 * | 1/2007 | Errico et al. | 623/17.15 |
| 7,172,628 B2 * | 2/2007 | Lamprich et al. | 623/17.16 |
| 7,204,851 B2 * | 4/2007 | Trieu et al. | 623/17.11 |
| 7,235,081 B2 * | 6/2007 | Errico et al. | 606/99 |
| 7,235,082 B2 * | 6/2007 | Bartish et al. | 606/99 |
| 7,252,673 B2 * | 8/2007 | Lim | 606/99 |
| 7,294,134 B2 * | 11/2007 | Weber | 606/99 |
| 7,320,689 B2 * | 1/2008 | Keller | 606/99 |
| 7,338,526 B2 * | 3/2008 | Steinberg | 623/17.12 |
| 7,384,431 B2 * | 6/2008 | Berry | 623/17.15 |
| 7,387,635 B2 * | 6/2008 | Keller | 606/99 |
| 7,404,795 B2 * | 7/2008 | Ralph et al. | 600/219 |
| 7,419,505 B2 * | 9/2008 | Fleischmann et al. | 623/17.11 |
| 7,530,982 B1 * | 5/2009 | Goshert | 606/95 |
| 7,547,309 B2 * | 6/2009 | Bertagnoli et al. | 606/99 |
| 7,549,995 B2 * | 6/2009 | Schultz | 606/99 |
| 7,572,281 B2 * | 8/2009 | Runco et al. | 606/279 |
| 7,575,580 B2 * | 8/2009 | Lim et al. | 606/99 |
| 7,582,114 B2 * | 9/2009 | Albert et al. | 623/17.13 |
| 7,588,573 B2 * | 9/2009 | Berry | 606/86 A |
| 7,594,919 B2 * | 9/2009 | Peterman | 606/99 |
| 7,608,078 B2 * | 10/2009 | Berry | 606/86 A |
| 7,618,423 B1 * | 11/2009 | Valentine et al. | 606/99 |
| 7,625,379 B2 * | 12/2009 | Puno et al. | 606/99 |
| 7,625,380 B2 * | 12/2009 | Drewry et al. | 606/99 |
| 7,632,281 B2 * | 12/2009 | Errico et al. | 606/99 |
| 7,648,506 B2 * | 1/2010 | McCord et al. | 606/86 A |
| 7,651,500 B2 * | 1/2010 | Supper et al. | 606/90 |
| 7,674,296 B2 * | 3/2010 | Rhoda et al. | 623/17.15 |
| 7,695,478 B2 * | 4/2010 | Ralph et al. | 606/99 |
| 7,722,622 B2 * | 5/2010 | Evans et al. | 606/99 |
| 7,749,231 B2 * | 7/2010 | Bonvallet et al. | 606/99 |
| 7,780,675 B2 * | 8/2010 | Schneid | 606/99 |
| 7,803,162 B2 * | 9/2010 | Marnay et al. | 606/99 |
| 7,803,191 B2 * | 9/2010 | Biedermann et al. | 623/17.16 |
| 7,806,901 B2 * | 10/2010 | Stad et al. | 606/99 |
| 7,811,287 B2 * | 10/2010 | Errico et al. | 606/86 A |
| 7,819,921 B2 * | 10/2010 | Grotz | 623/17.11 |
| 7,819,922 B2 | 10/2010 | Sweeney | |
| 7,824,413 B2 * | 11/2010 | Varieur et al. | 606/99 |
| 7,824,427 B2 * | 11/2010 | Perez-Cruet et al. | 606/246 |
| 7,842,043 B2 * | 11/2010 | Errico et al. | 606/99 |
| 7,842,044 B2 * | 11/2010 | Runco et al. | 606/104 |
| 7,846,210 B2 * | 12/2010 | Perez-Cruet et al. | 623/17.16 |
| 7,879,096 B2 * | 2/2011 | Dickson et al. | 623/17.11 |

(56) References Cited

U.S. PATENT DOCUMENTS

| | | | |
|---|---|---|---|
| 7,892,173 B2* | 2/2011 | Miles et al. | 600/210 |
| 7,892,239 B2* | 2/2011 | Warnick et al. | 606/99 |
| 7,896,884 B2* | 3/2011 | Wing et al. | 606/90 |
| 7,901,458 B2* | 3/2011 | DeRidder et al. | 623/17.11 |
| 7,914,581 B2* | 3/2011 | Dickson et al. | 623/17.16 |
| 7,918,888 B2* | 4/2011 | Hamada | 623/17.11 |
| 7,927,373 B2* | 4/2011 | Parsons et al. | 623/17.14 |
| 7,931,654 B2* | 4/2011 | Jones et al. | 606/86 A |
| 7,981,157 B2* | 7/2011 | Castleman et al. | 623/17.15 |
| 8,012,156 B2* | 9/2011 | Marquez Alvarez | 606/99 |
| 8,025,665 B2* | 9/2011 | Lim et al. | 606/90 |
| 8,038,715 B2* | 10/2011 | Kim et al. | 623/17.13 |
| 8,043,377 B2* | 10/2011 | Guyer et al. | 623/17.11 |
| 8,048,084 B2* | 11/2011 | Schneid | 606/99 |
| 8,062,303 B2* | 11/2011 | Berry et al. | 606/90 |
| 8,097,027 B2* | 1/2012 | Lim et al. | 606/279 |
| 8,105,328 B2* | 1/2012 | Protopsaltis | 606/86 A |
| 8,105,382 B2* | 1/2012 | Olmos et al. | 623/17.15 |
| 8,114,088 B2* | 2/2012 | Miller | 606/90 |
| 8,114,092 B2* | 2/2012 | Altarac et al. | 606/99 |
| 8,123,757 B2* | 2/2012 | Zalenski et al. | 606/99 |
| 8,137,356 B2* | 3/2012 | Hestad et al. | 606/86 A |
| 8,142,435 B2* | 3/2012 | Refai et al. | 606/86 A |
| 8,142,441 B2* | 3/2012 | Refai et al. | 606/99 |
| 8,167,885 B2* | 5/2012 | Barrett | 606/86 A |
| 8,206,399 B2* | 6/2012 | Gill et al. | 606/99 |
| 8,206,449 B2* | 6/2012 | Jansen et al. | 623/17.16 |
| 8,216,241 B2* | 7/2012 | Runco et al. | 606/86 A |
| 8,231,633 B2* | 7/2012 | Lim et al. | 606/99 |
| 8,241,294 B2* | 8/2012 | Sommerich et al. | 606/90 |
| 8,298,241 B2* | 10/2012 | Arnhold | 606/99 |
| 8,308,734 B2* | 11/2012 | Evans et al. | 606/99 |
| 8,328,818 B1* | 12/2012 | Seifert et al. | 606/105 |
| 8,337,500 B2* | 12/2012 | Bertagnoli et al. | 606/80 |
| 8,343,163 B1* | 1/2013 | Arambula et al. | 606/99 |
| 8,343,164 B2* | 1/2013 | Wallenstein et al. | 606/99 |
| 8,343,219 B2* | 1/2013 | Allain et al. | 623/17.11 |
| 8,348,958 B2* | 1/2013 | Ralph et al. | 606/99 |
| 8,377,071 B2* | 2/2013 | Lim et al. | 606/90 |
| 8,377,072 B2* | 2/2013 | Stad et al. | 606/99 |
| 8,382,767 B2* | 2/2013 | Wassinger et al. | 606/99 |
| 8,382,768 B2* | 2/2013 | Berry et al. | 606/99 |
| 8,486,083 B2* | 7/2013 | Puno et al. | 606/99 |
| 2001/0005796 A1* | 6/2001 | Zdeblick et al. | 623/17.11 |
| 2002/0058944 A1* | 5/2002 | Michelson | 606/79 |
| 2002/0058950 A1* | 5/2002 | Winterbottom et al. | 606/99 |
| 2002/0068978 A1* | 6/2002 | Camino et al. | 623/17.16 |
| 2002/0072752 A1* | 6/2002 | Zucherman et al. | 606/99 |
| 2002/0082695 A1* | 6/2002 | Neumann | 623/17.11 |
| 2002/0116009 A1* | 8/2002 | Fraser et al. | 606/99 |
| 2002/0161441 A1* | 10/2002 | Lang et al. | 623/17.11 |
| 2003/0045877 A1* | 3/2003 | Yeh | 606/61 |
| 2003/0083747 A1* | 5/2003 | Winterbottom et al. | 623/17.11 |
| 2003/0135220 A1* | 7/2003 | Cauthen | 606/87 |
| 2003/0191531 A1 | 10/2003 | Berry | |
| 2003/0236520 A1* | 12/2003 | Lim et al. | 606/61 |
| 2004/0030346 A1* | 2/2004 | Frey et al. | 606/99 |
| 2004/0049271 A1* | 3/2004 | Biedermann et al. | 623/17.11 |
| 2004/0059271 A1* | 3/2004 | Berry | 602/32 |
| 2004/0059318 A1* | 3/2004 | Zhang et al. | 606/1 |
| 2004/0093083 A1* | 5/2004 | Branch et al. | 623/17.11 |
| 2004/0102790 A1* | 5/2004 | Ralph et al. | 606/99 |
| 2004/0133280 A1* | 7/2004 | Trieu | 623/17.16 |
| 2004/0147936 A1* | 7/2004 | Rosenberg et al. | 606/99 |
| 2004/0148028 A1* | 7/2004 | Ferree et al. | 623/17.11 |
| 2004/0153160 A1* | 8/2004 | Carrasco | 623/17.15 |
| 2004/0167537 A1* | 8/2004 | Errico et al. | 606/99 |
| 2004/0172129 A1* | 9/2004 | Schafer et al. | 623/17.11 |
| 2004/0181283 A1* | 9/2004 | Boyer et al. | 623/17.11 |
| 2004/0186569 A1* | 9/2004 | Berry | 623/17.11 |
| 2004/0186576 A1* | 9/2004 | Biscup et al. | 623/17.12 |
| 2004/0193158 A1* | 9/2004 | Lim et al. | 606/61 |
| 2004/0210312 A1* | 10/2004 | Neumann | 623/17.11 |
| 2004/0220582 A1* | 11/2004 | Keller | 606/99 |
| 2005/0015095 A1* | 1/2005 | Keller | 606/99 |
| 2005/0021042 A1* | 1/2005 | Marnay et al. | 606/99 |
| 2005/0033305 A1* | 2/2005 | Schultz | 606/99 |
| 2005/0038445 A1* | 2/2005 | Errico et al. | 606/99 |
| 2005/0060036 A1* | 3/2005 | Schultz et al. | 623/17.15 |
| 2005/0085910 A1* | 4/2005 | Sweeney | 623/17.11 |
| 2005/0090824 A1* | 4/2005 | Shluzas et al. | 606/61 |
| 2005/0090898 A1* | 4/2005 | Berry et al. | 623/17.11 |
| 2005/0113921 A1* | 5/2005 | An et al. | 623/17.11 |
| 2005/0143749 A1* | 6/2005 | Zalenski et al. | 606/99 |
| 2005/0159756 A1* | 7/2005 | Ray | 606/87 |
| 2005/0165408 A1* | 7/2005 | Puno et al. | 606/99 |
| 2005/0187634 A1* | 8/2005 | Berry | 623/17.15 |
| 2005/0203538 A1* | 9/2005 | Lo et al. | 606/99 |
| 2005/0216084 A1* | 9/2005 | Fleischmann et al. | 623/17.11 |
| 2005/0234550 A1* | 10/2005 | Metz-Stavenhagen | 623/17.11 |
| 2006/0004376 A1* | 1/2006 | Shipp et al. | 606/99 |
| 2006/0004377 A1* | 1/2006 | Keller | 606/99 |
| 2006/0004447 A1* | 1/2006 | Mastrorio et al. | 623/17.11 |
| 2006/0030860 A1* | 2/2006 | Peterman | 606/99 |
| 2006/0052793 A1* | 3/2006 | Heinz | 606/90 |
| 2006/0058808 A1* | 3/2006 | Schneid | 606/99 |
| 2006/0058877 A1* | 3/2006 | Gutlin et al. | 623/17.11 |
| 2006/0058879 A1* | 3/2006 | Metz-Stavenhagen | 623/17.15 |
| 2006/0074488 A1* | 4/2006 | Abdou | 623/17.11 |
| 2006/0074490 A1* | 4/2006 | Sweeney | 623/17.15 |
| 2006/0085011 A1* | 4/2006 | Filippi et al. | 606/99 |
| 2006/0085073 A1* | 4/2006 | Raiszadeh | 623/17.12 |
| 2006/0100710 A1* | 5/2006 | Gutlin et al. | 623/17.15 |
| 2006/0122701 A1* | 6/2006 | Kiester | 623/17.11 |
| 2006/0142859 A1* | 6/2006 | McLuen | 623/17.11 |
| 2006/0149284 A1* | 7/2006 | McCormack et al. | 606/99 |
| 2006/0149371 A1* | 7/2006 | Marik et al. | 623/17.11 |
| 2006/0200244 A1* | 9/2006 | Assaker | 623/17.15 |
| 2006/0224241 A1* | 10/2006 | Butler et al. | 623/17.15 |
| 2006/0235426 A1* | 10/2006 | Lim et al. | 606/99 |
| 2006/0235521 A1* | 10/2006 | Zucherman et al. | 623/17.11 |
| 2006/0241762 A1* | 10/2006 | Kraus | 623/17.11 |
| 2006/0241770 A1* | 10/2006 | Rhoda et al. | 623/17.15 |
| 2006/0293755 A1* | 12/2006 | Lindner et al. | 623/17.15 |
| 2007/0016221 A1* | 1/2007 | Beyersdorff et al. | 606/99 |
| 2007/0093850 A1* | 4/2007 | Harris et al. | 606/99 |
| 2007/0093901 A1* | 4/2007 | Grotz et al. | 623/17.11 |
| 2007/0118145 A1* | 5/2007 | Fischer et al. | 606/99 |
| 2007/0123903 A1* | 5/2007 | Raymond et al. | 606/99 |
| 2007/0123904 A1* | 5/2007 | Stad et al. | 606/99 |
| 2007/0123905 A1* | 5/2007 | Schneid | 606/99 |
| 2007/0123907 A1* | 5/2007 | Weber | 606/99 |
| 2007/0129805 A1* | 6/2007 | Braddock et al. | 623/17.11 |
| 2007/0173855 A1* | 7/2007 | Winn et al. | 606/90 |
| 2007/0191860 A1* | 8/2007 | Heinz et al. | 606/99 |
| 2007/0191954 A1* | 8/2007 | Hansell et al. | 623/17.15 |
| 2007/0203490 A1* | 8/2007 | Zucherman et al. | 606/60 |
| 2007/0233152 A1* | 10/2007 | Stad et al. | 606/99 |
| 2007/0233153 A1* | 10/2007 | Shipp et al. | 606/99 |
| 2007/0233254 A1* | 10/2007 | Grotz et al. | 623/17.11 |
| 2007/0250171 A1* | 10/2007 | Bonin, Jr. | 623/17.15 |
| 2007/0255407 A1* | 11/2007 | Castleman et al. | 623/17.11 |
| 2007/0255408 A1* | 11/2007 | Castleman et al. | 623/17.11 |
| 2007/0255410 A1* | 11/2007 | Dickson et al. | 623/17.11 |
| 2007/0255413 A1* | 11/2007 | Edie et al. | 623/17.16 |
| 2007/0255421 A1* | 11/2007 | Dickson | 623/23.47 |
| 2007/0282372 A1* | 12/2007 | Yedlicka et al. | 606/205 |
| 2008/0004705 A1* | 1/2008 | Rogeau et al. | 623/17.16 |
| 2008/0015609 A1* | 1/2008 | Trautwein et al. | 606/99 |
| 2008/0021555 A1* | 1/2008 | White et al. | 623/17.11 |
| 2008/0021556 A1* | 1/2008 | Edie | 623/17.11 |
| 2008/0039860 A1* | 2/2008 | Trudeau | 606/99 |
| 2008/0045968 A1* | 2/2008 | Yu et al. | 606/99 |
| 2008/0051896 A1* | 2/2008 | Suddaby | 623/17.12 |
| 2008/0058931 A1* | 3/2008 | White et al. | 623/17.11 |
| 2008/0077153 A1* | 3/2008 | Pernsteiner et al. | 606/99 |
| 2008/0140207 A1* | 6/2008 | Olmos et al. | 623/17.16 |
| 2008/0154305 A1* | 6/2008 | Foley et al. | 606/247 |
| 2008/0161817 A1* | 7/2008 | Parsons et al. | 606/90 |
| 2008/0167726 A1* | 7/2008 | Melkent | 623/23.48 |
| 2008/0177275 A1* | 7/2008 | Wing et al. | 606/99 |
| 2008/0243254 A1* | 10/2008 | Butler | 623/17.16 |
| 2008/0255574 A1* | 10/2008 | Dye | 606/99 |
| 2008/0262504 A1* | 10/2008 | Ralph et al. | 606/99 |

(56) References Cited

U.S. PATENT DOCUMENTS

| | | | | |
|---|---|---|---|---|
| 2008/0269764 | A1* | 10/2008 | Blain et al. | 606/99 |
| 2008/0269899 | A1* | 10/2008 | Horton | 623/17.15 |
| 2008/0275455 | A1* | 11/2008 | Berry et al. | 606/99 |
| 2008/0287957 | A1* | 11/2008 | Hester et al. | 606/99 |
| 2008/0288071 | A1* | 11/2008 | Biyani et al. | 623/17.11 |
| 2008/0288073 | A1* | 11/2008 | Renganath et al. | 623/17.12 |
| 2008/0306488 | A1* | 12/2008 | Altarac et al. | 606/99 |
| 2009/0005874 | A1* | 1/2009 | Fleischmann et al. | 623/17.16 |
| 2009/0030419 | A1* | 1/2009 | Runco et al. | 606/99 |
| 2009/0030421 | A1* | 1/2009 | Hawkins et al. | 606/99 |
| 2009/0030422 | A1* | 1/2009 | Parsons et al. | 606/99 |
| 2009/0048604 | A1* | 2/2009 | Milz et al. | 606/99 |
| 2009/0048673 | A1* | 2/2009 | Le Huec | 623/17.11 |
| 2009/0076607 | A1* | 3/2009 | Aalsma et al. | 623/17.16 |
| 2009/0076610 | A1* | 3/2009 | Afzal | 623/17.16 |
| 2009/0105832 | A1* | 4/2009 | Allain et al. | 623/17.16 |
| 2009/0112217 | A1* | 4/2009 | Hester | 606/99 |
| 2009/0112220 | A1* | 4/2009 | Kraus | 606/99 |
| 2009/0112324 | A1* | 4/2009 | Refai et al. | 623/17.16 |
| 2009/0112325 | A1* | 4/2009 | Refai et al. | 623/17.16 |
| 2009/0138091 | A1* | 5/2009 | Ray | 623/17.16 |
| 2009/0171363 | A1* | 7/2009 | Chocron | 606/99 |
| 2009/0177285 | A1* | 7/2009 | Frey et al. | 623/17.16 |
| 2009/0192611 | A1* | 7/2009 | Lindner | 623/17.11 |
| 2009/0198246 | A1* | 8/2009 | Lim et al. | 606/99 |
| 2009/0209967 | A1* | 8/2009 | Evans et al. | 606/99 |
| 2009/0216331 | A1* | 8/2009 | Grotz et al. | 623/17.16 |
| 2009/0240254 | A1* | 9/2009 | Arnhold | 606/99 |
| 2009/0292361 | A1* | 11/2009 | Lopez | 623/17.15 |
| 2009/0306672 | A1* | 12/2009 | Reindel et al. | 606/90 |
| 2009/0326542 | A9* | 12/2009 | Errico et al. | 606/99 |
| 2010/0016972 | A1* | 1/2010 | Jansen et al. | 623/17.16 |
| 2010/0023019 | A1* | 1/2010 | Fuhrer et al. | 606/99 |
| 2010/0069914 | A1* | 3/2010 | Puno et al. | 606/99 |
| 2010/0076557 | A1* | 3/2010 | Miller | 623/17.11 |
| 2010/0100100 | A1* | 4/2010 | Refai et al. | 606/99 |
| 2010/0114105 | A1* | 5/2010 | Butters et al. | 606/99 |
| 2010/0174371 | A9* | 7/2010 | Errico et al. | 623/17.11 |
| 2010/0185285 | A1* | 7/2010 | Perkins | 623/17.11 |
| 2010/0211119 | A1* | 8/2010 | Refai et al. | 606/86 A |
| 2010/0217272 | A1* | 8/2010 | Baughman et al. | 606/99 |
| 2010/0249792 | A1* | 9/2010 | Bonvallet et al. | 606/90 |
| 2010/0249795 | A1* | 9/2010 | DiMauro et al. | 606/99 |
| 2011/0015638 | A1* | 1/2011 | Pischl et al. | 606/90 |
| 2011/0087328 | A1* | 4/2011 | Dickson et al. | 623/17.11 |
| 2011/0106261 | A1* | 5/2011 | Chin et al. | 623/17.16 |
| 2011/0202135 | A1* | 8/2011 | Baek et al. | 623/17.16 |
| 2011/0270261 | A1* | 11/2011 | Mast et al. | 606/99 |
| 2011/0301612 | A1* | 12/2011 | Richter et al. | 606/99 |
| 2012/0265211 | A1* | 10/2012 | Lim et al. | 606/99 |

FOREIGN PATENT DOCUMENTS

| | | |
|---|---|---|
| DE | 40 12 622 | 7/1991 |
| DE | 41 09 941 | 10/1992 |
| DE | 44 09 392 | 3/1994 |
| DE | 44 23 257 | 1/1996 |
| DE | 19 500 170 | 2/1996 |
| DE | 19 509 317 | 9/1996 |
| DE | 19 519 101 | 11/1996 |
| DE | 196 22 827 | 12/1997 |
| DE | 296 16 778 | 3/1998 |
| DE | 91 07 494 | 10/1998 |
| DE | 198 04 765 | 8/1999 |
| DE | 202 130 13 | 1/2003 |
| DE | 10 357 926 | 9/2005 |
| DE | 203 20 974 | 2/2007 |
| DE | 20 2008 001 261 | 4/2008 |
| EP | 0 188 954 | 7/1986 |
| EP | 0 290 767 | 11/1988 |
| EP | 0 490 159 | 6/1992 |
| EP | 0 567 424 | 10/1993 |
| EP | 0 832 622 | 4/1998 |
| EP | 0 968 692 | 1/2000 |
| EP | 1 080 703 | 3/2001 |
| EP | 1 188 424 | 3/2002 |
| EP | 1 219 266 | 3/2002 |
| EP | 1 219 266 | 7/2002 |
| EP | 1 459 710 | 9/2004 |
| EP | 1491165 | 12/2004 |
| EP | 1 867 304 | 12/2007 |
| JP | 62 164458 | 7/1997 |
| SU | 1 560 184 | 4/1990 |
| SU | 1 739 989 | 6/1992 |
| WO | WO 92 01428 | 2/1992 |
| WO | WO 94 18913 | 9/1994 |
| WO | WO 9525486 | 9/1995 |
| WO | WO 96 17564 | 6/1996 |
| WO | WO 96 37170 | 11/1996 |
| WO | WO 97 47258 | 12/1997 |
| WO | WO 98 46173 | 10/1998 |
| WO | WO 99 39665 | 8/1999 |
| WO | WO 99 56675 | 11/1999 |
| WO | WO 99 63913 | 12/1999 |
| WO | WO 00 23013 | 4/2000 |
| WO | WO 03 096937 | 11/2003 |
| WO | WO 2004 019827 | 3/2004 |
| WO | WO 2004 026157 | 4/2004 |
| WO | WO 2004 093751 | 4/2004 |
| WO | WO 2004 052245 | 6/2004 |
| WO | WO 2004 096103 | 11/2004 |
| WO | WO 2004 100837 | 11/2004 |
| WO | WO 2005 055887 | 6/2005 |
| WO | WO 2006 065910 | 6/2006 |
| WO | WO 2007 076261 | 7/2007 |
| WO | WO 2008/065450 | 6/2008 |
| WO | WO 2009 058576 | 5/2009 |

OTHER PUBLICATIONS

U.S. Appl. No. 12/252,552, Non-Final Office Action mailed Sep. 6, 2011, 6 pgs.

U.S. Patent and Trademark Office Non-Final Office Action Issued for U.S. Appl. No. 11/928,553 Dated Jul. 31, 2012.

Search Report and Written Opinion for International Application PCT/US2010/022805, Dated Jun. 24, 2010.

Office Action dated Aug. 26, 2011 for U.S. Appl. No. 12/388,581.

Final Office Action Dated Mar. 17, 2011 for U.S. Appl. No. 11/928,553.

Refai et al., PCT Search Report and Written Opinion Dated Feb. 24, 2009. PCT/US2008/080143, 14 pgs.

PCT Search Report and Written Opinion Mailed Feb. 17, 2010. PCT/US2009/060608, 17 pgs.

PCT Search Report and Written Opinion Mailed Feb. 23, 2009. PCT/US2008/080127, 17 pgs.

U.S. Appl. No. 11/928,553, Final Office Action mailed Feb. 15, 2013, 14 pgs.

Office Action for U.S. Appl. No. 13/475,279 dated Apr. 8, 2013.

Office Action for U.S. Appl. No. 11/928,553 dated Dec. 7, 2010.

Official Action for European Application No. 08 844 082.1 dated May 18, 2012.

English Translation of Office Action for Japanese Application No. 2010-531138 dated Jun. 12, 2012.

* cited by examiner

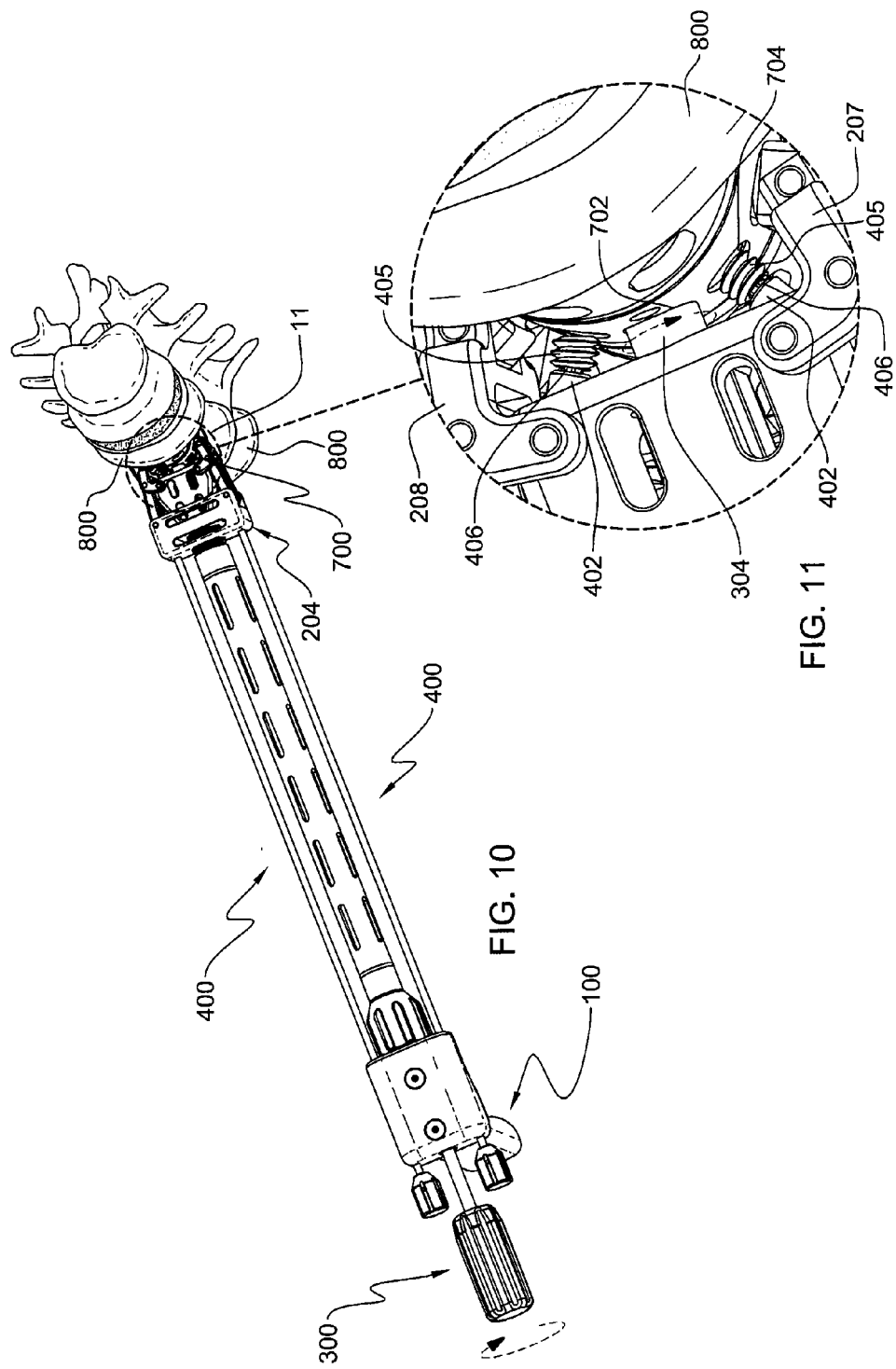

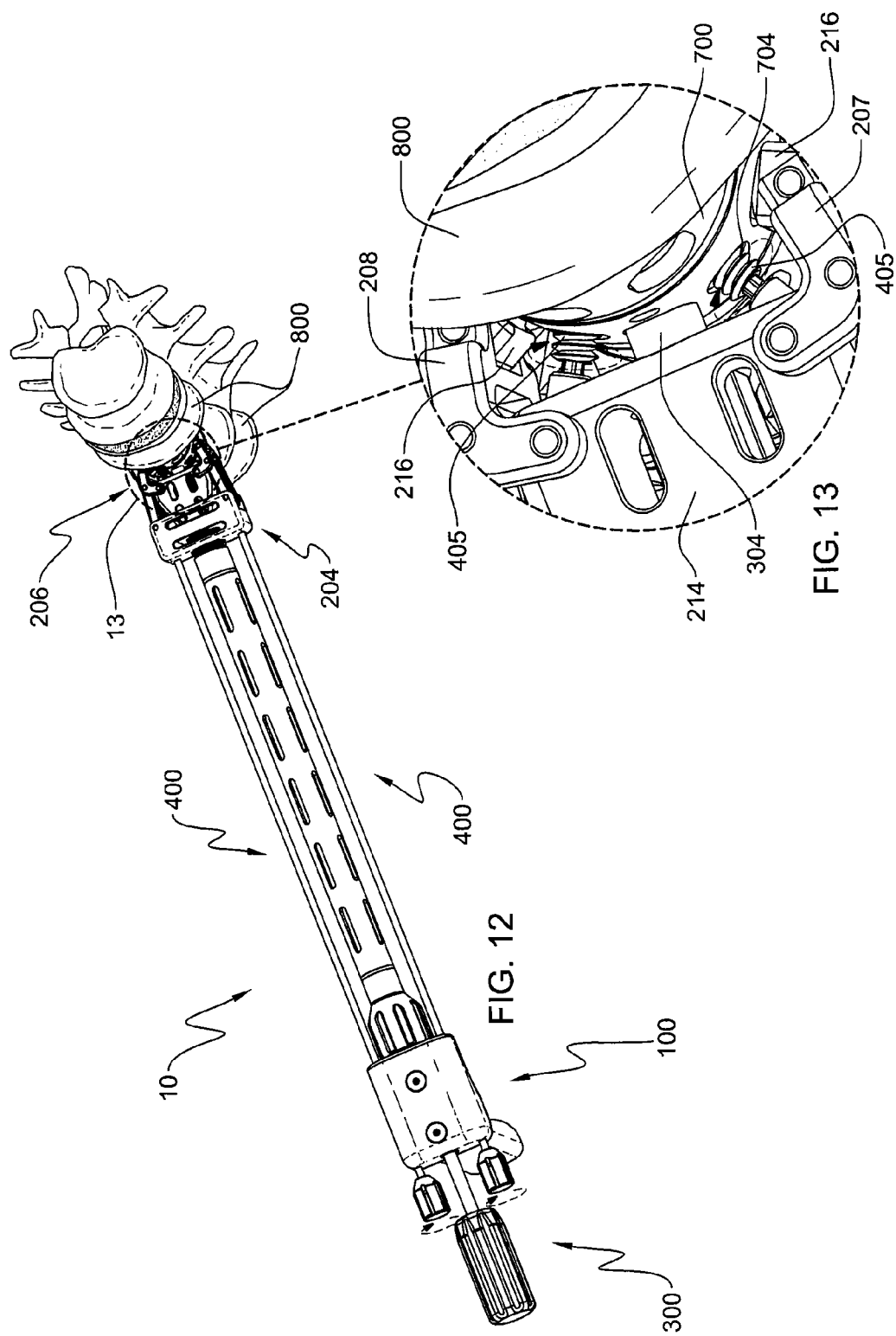

SURGICAL INSTRUMENT AND METHOD OF USE FOR INSERTING AN IMPLANT BETWEEN TWO BONES

RELATED APPLICATIONS

This application is a continuation of U.S. application Ser. No. 12/252,552, filed Oct. 16, 2008, the contents of which are incorporated by reference herein in its entirety and for all purposes.

TECHNICAL FIELD

The present invention relates generally to orthopaedic and neurosurgical instrumentation and techniques, and more specifically, but not exclusively, concerns an inserter to be used to implant a device between two bones.

BACKGROUND OF THE INVENTION

Damage or disease that affects the integral structure of a bone structure or more specifically, a vertebral body within an individual's spinal column may lead to neurologic impairment with possible permanent damage to the surrounding tissue. Maintaining proper anatomic spacing within a bone structure and the spinal column is, critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. A need remains for a multipurpose instrument to be used to implant a spacer type of implant that allows the surgeon to minimize the size of the surgical incision, facilitate the operative technique and decrease patient morbidity.

SUMMARY OF THE INVENTION

Advancement of the state of the surgical instrumentation that are used to implant devices between two bones and more specifically, spinal implants for use in the surgical management of patients with missing or damaged vertebral bodies within an intact spinal column is believed desirable. The present invention satisfies the need for improvements to surgical instruments used to insert and adjust bone spacer devices and implants, but more specifically, vertebral spacer devices that are implanted in patients suffering from either diseased or damaged vertebral bodies by providing a multi-functional instrument that allows the operating surgeon to grasp, change the length and secure a variable length vertebral body replacement device following insertion into the wound site and spinal column.

The present invention provides in one aspect, a surgical instrument for inserting an implant between two bones that includes a handle and an elongate member that has a first end and a second end, and a longitudinal axis extending between these two ends with the second end being moveably connected to an implant engagement assembly that is positioned at a distal end of the surgical instrument. The implant engagement assembly is configured to hold the implant. Movement of the elongate member relative to the implant engagement assembly results in the implant engagement assembly adjusting the implant to allow the operating surgeon to place the implant between the two bones.

The present invention provides in another aspect, a surgical instrument for inserting a spinal implant between two vertebrae that includes a handle assembly at the proximal end of the surgical instrument and an elongate member that has a first end and a second end with a longitudinal axis extending between the two ends. The first end is located adjacent to the handle assembly and the second end is configured to be rotationably connected to the spinal implant engagement assembly that is positioned at the distal end of the surgical instrument. The surgical instrument also includes a length control mechanism for adjusting the overall length of the spinal implant when the spinal implant has been placed between two vertebrae. The length control mechanism is constructed with a gripping portion, a gear assembly and a drive shaft that is positioned intermediate the gripping portion and gear assembly. The drive shaft extends through a first opening within the handle assembly and is oriented substantially parallel to the longitudinal axis of the elongate member. The surgical instrument further includes a first locking mechanism for securing the overall length of the spinal implant after the spinal implant has been placed between the two vertebrae. The first locking mechanism has a gripping portion proximate to the proximal end of the surgical instrument, a coupling end and a connecting rod that is intermediate the gripping portion and the coupling end. The connecting rod extends through a second opening in the handle assembly and is oriented substantially parallel to the longitudinal axis of the elongate member.

The present invention provides in yet another aspect, a surgical method for inserting an implant between two bones that includes the step of surgically creating an opening on the skin of a patient that is proximate the location of the two bones. The method further includes the step of obtaining a surgical instrument that has a handle assembly, an elongate member that has a first end and a second end, and a longitudinal axis that extends between the two ends. The first end is positioned adjacent to the handle assembly and the second end is being moveably connected to the implant engagement assembly that is located at the distal end of the surgical instrument. The surgical instrument also has a length control mechanism for adjusting the overall length of the implant when the implant has been placed between the two bones with the length control mechanism having a gripping portion, a gear assembly and a drive shaft that is intermediate the gripping portion and gear assembly. The drive shaft is configured to extend through a first opening within the handle assembly and is oriented substantially parallel to the longitudinal axis of the elongate member. The surgical instrument further includes at least one locking mechanism for securing the overall length of the implant after the implant has been placed between the two bones. The at least one locking mechanism has a gripping portion proximate to the proximal end of the surgical instrument, a coupling end and a connecting rod that is intermediate the gripping portion and the coupling end. The connecting rod extends through a second opening in the handle assembly and is oriented substantially parallel to the longitudinal axis of the elongate member. The surgical method usually includes the further steps of coupling the implant to the implant engagement assembly and then inserting the surgical instrument and coupled implant into the skin opening. The surgical method may further include the step of positioning the implant into the space between the two bones. Yet a further step of the method may be to extend the implant to an overall length that causes the implant to contact and apply a force to the two bones to maintain the space between the two bones. The surgical method typically includes another step of fixing or securing the overall length of the inserted implant.

The present invention provides in another aspect a method of fabricating a surgical instrument. The method may include the step of providing a handle assembly. The method of fabrication may include the further step of providing an elongate member that has a first end and a second end with a longitudinal axis extending between the two ends. The first end is positioned adjacent to the handle assembly and the second end is moveably connected to the implant engagement assembly that is located at the distal end of the surgical instrument. Movement of the elongate member relative to the handle assembly and the implant engagement assembly results in the implant engagement assembly being coupled to the implant to allow for placement of the implant between the two bones.

Yet a further aspect of the present invention provides a spinal implant insertion kit that includes a spinal implant that is to be placed between two vertebrae and a surgical instrument that has a handle assembly and an elongate member that has a first end and a second end with a longitudinal axis extending between the two ends. The first end is positioned adjacent to the handle assembly and the second end is moveably connected to the spinal implant engagement assembly that is at the distal end of the surgical instrument. The surgical instrument also has a length control mechanism for adjusting the overall length of the spinal implant when the spinal implant has been placed between the two vertebrae. The length control mechanism has a gripping portion, a gear assembly and a drive shaft positioned intermediate the gripping portion and gear assembly with the drive shaft extending through a first opening within the handle assembly. The device shaft is also oriented substantially parallel to the longitudinal axis of the elongate member. The surgical instrument also includes at least one locking mechanism for securing the overall length of the spinal implant after the spinal implant has been placed between the two bones. The at least one locking mechanism has a gripping portion proximate to the proximal end of the surgical instrument, a coupling end and a connecting rod that is intermediate the gripping portion and the coupling end. The connecting rod extends through a second opening in the handle assembly and is oriented substantially parallel to the longitudinal axis of the elongate member.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

FIG. 10 is a perspective view of the spinal implant coupled to the surgical instrument of FIG. 1, shown positioned in a space between two vertebral bodies with the length control mechanism being rotated to extend the spinal implant to allow the ends to make contact with the superior and inferior vertebral bodies to maintain a desired spacing arrangement within a spinal column, in accordance with an aspect of the present invention;

FIG. 11 is an enlarged top view of distal end of the surgical instrument of FIG. 1, showing the gear assembly inserted into the spinal implant, in accordance with an aspect of the present invention;

FIG. 12 is a perspective view of the spinal implant coupled to the surgical instrument of FIG. 1, shown positioned in a space between two vertebral bodies following final length determination with the locking mechanism being rotated, in accordance with an aspect of the present invention; and FIG. 13 is an enlarged top view of the distal end of the surgical instrument of FIG. 1, showing the coupling end and attached locking pin/screw being inserted into the spinal implant, in accordance with an aspect of the present invention.

DETAILED DESCRIPTION FOR CARRYING OUT THE INVENTION

Generally stated, disclosed herein is a surgical instrument for use in inserting an implant into a space between two bones. More specifically, the surgical instrument will typically be used to hold, extend/contract and lock a vertebral body replacement implant during implantation into the spinal column. The surgical instrument generally includes a handle assembly, an elongate member that includes an implant engagement assembly at the distal end. The implant engagement assembly further includes an actuation body and an implant holding portion that has two arms that move and grasp the implant when the actuation body is actuated. The surgical instrument further includes a length control mechanism and locking mechanism. The distal end or gear assembly of the length control mechanism is inserted into the implant and couples to a corresponding length adjustment mechanism to allow for varying the overall length of the implant. The surgical instrument typically further includes a locking mechanism that provides for the insertion of a locking pin or screw into the implant to fix the overall length of the implant.

As used herein, the terms "surgical instrument" and "inserter" may be used interchangeably as they essentially describe the same type of operative instrument. Further, described herein is a surgical method for using the surgical instrument, a method of fabricating the surgical instrument and a spinal implant insertion kit that is used to maintain a space between two vertebrae within a patient suffering from a diseased or damaged spinal column.

Figure 1:
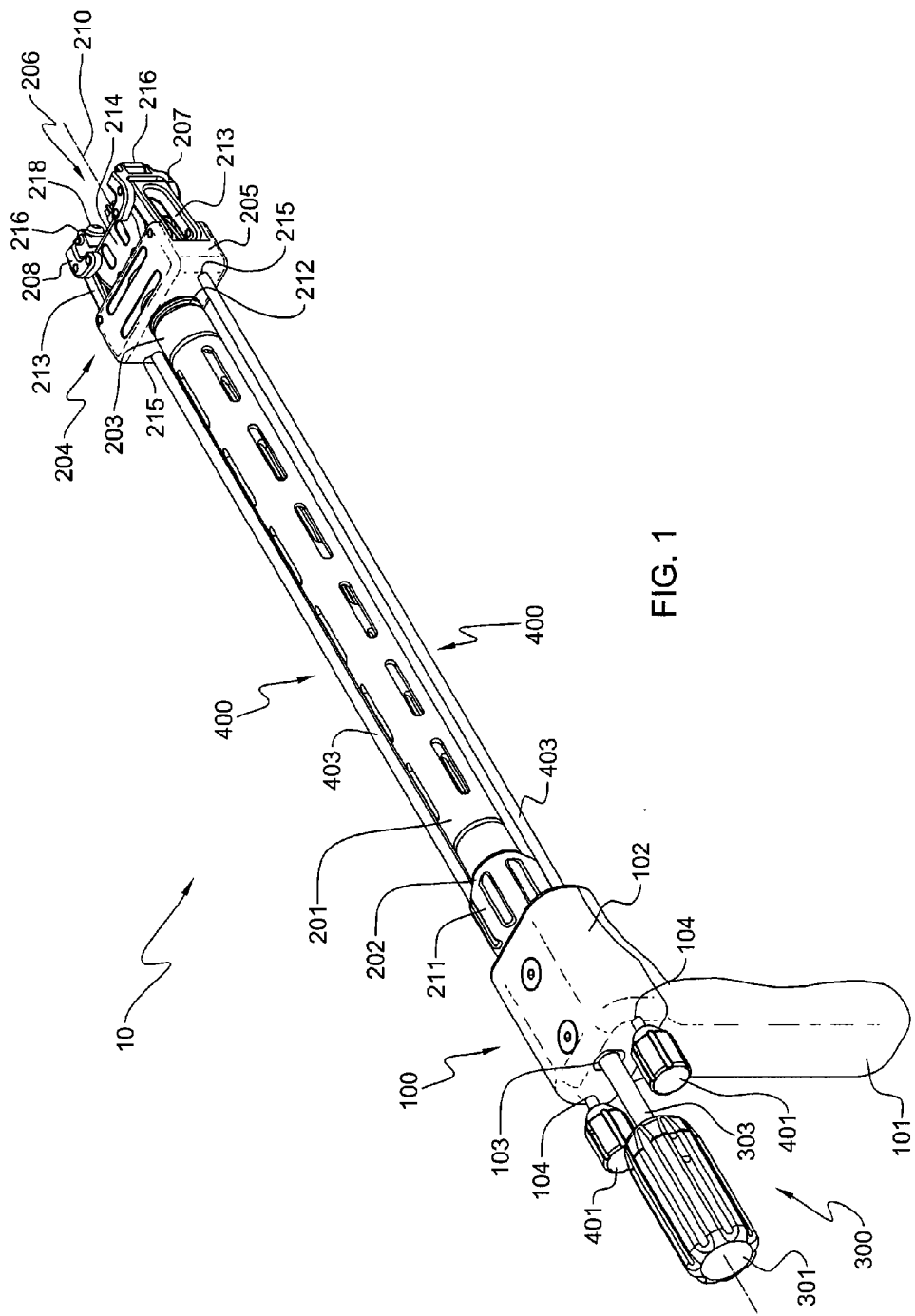
FIG. 1 is a perspective view of one embodiment of a surgical instrument, in accordance with an aspect of the present invention.
Figure 3:
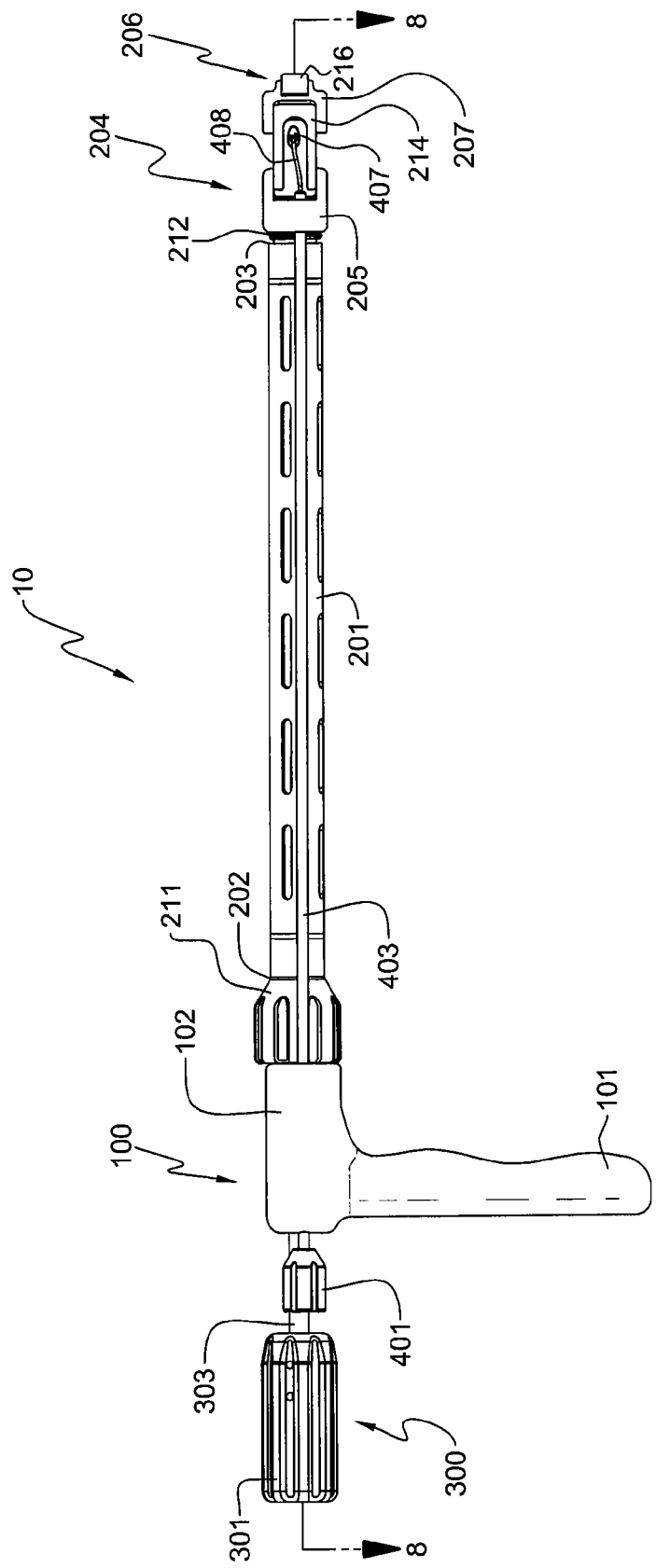
FIG. 3 is a side elevational view of the surgical instrument of FIG. 1, in accordance with an aspect of the present invention.
Figure 4:
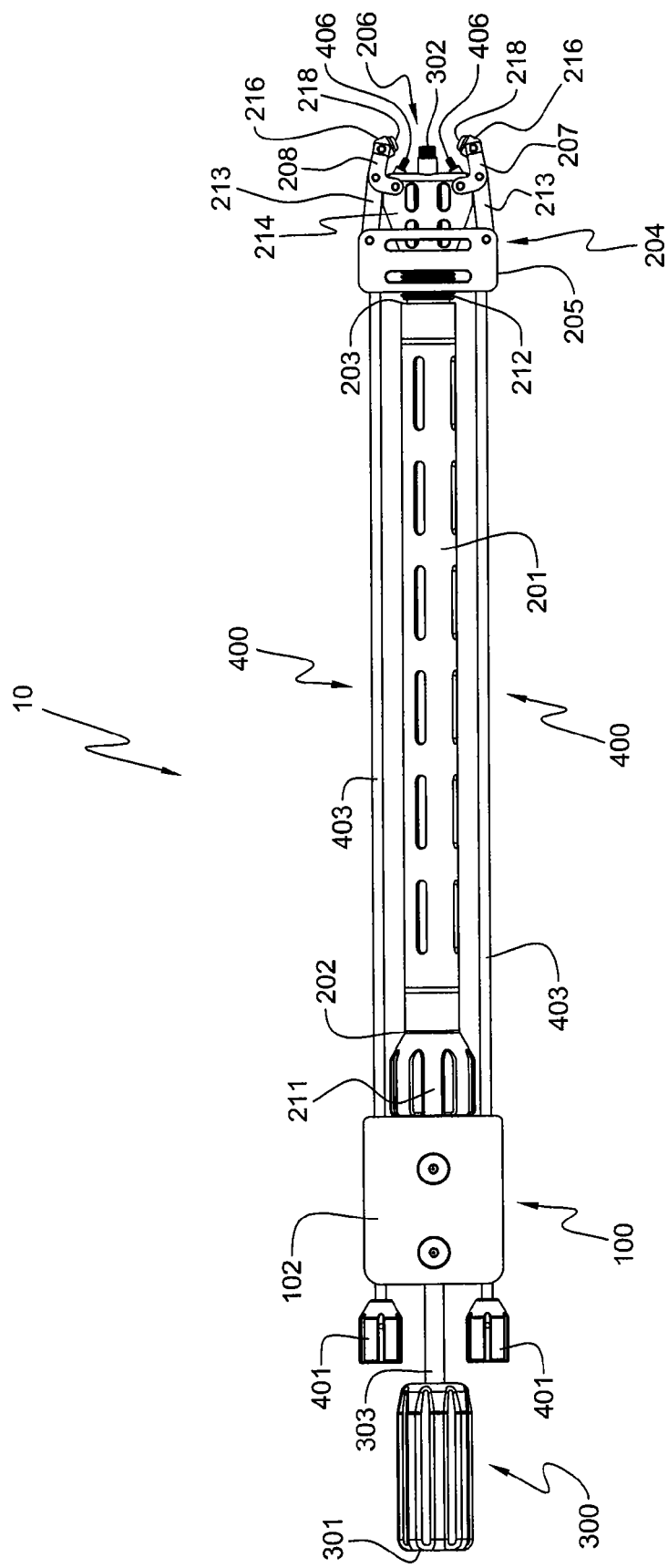
FIG. 4 is a top view of the surgical instrument of FIG. 1, in accordance with an aspect of the present invention.

As depicted in FIGS. 1, 3 and 4, the general arrangement of a surgical instrument 10, in accordance with an aspect of the present invention, includes a handle assembly 100, an elongate member 201, an implant engagement assembly 204, a length control mechanism 300, and at least one locking mechanism 400. Surgical instrument 10 is to be used to grasp, expand and contract the length and secure the overall length of the implant when placed within the body. One type of implant that may be used with surgical instrument 10 is the one described in co-pending U.S. patent application Ser. Nos. 11/928,532 and 11/928,553. The contents and disclosure provided in these two pending U.S. applications are hereby incorporated herein by reference.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

With reference to FIGS. 1 and 3, surgical instrument 10 includes handle assembly 100, elongate member 201, implant engagement assembly 204 that further includes an actuation body 205, an alignment body 214 and a holding portion 206. Further included in surgical instrument 10 is length control mechanism 300 and at least one locking mechanism 400 that is oriented to run parallel to a longitudinal axis 210 of elongate member 201.

As shown in FIG. 1, handle assembly 100 of surgical instrument 10 also includes a body portion 101 and a top portion 102. Body portion 101 is generally configured as a grip or holder to accommodate the palm and fingers of the operating surgeon. It is contemplated that body portion 101 may be available in varying sizes and configurations to allow for surgical instrument 10 to be used in a wide range of surgical applications, including endoscopic procedures and approaches as well as fit various user hand sizes without sacrificing dexterity and comfort. Centered in top portion and extending in proximal to distal direction is at least one through hole 103. Hole 103 is sized to receive and fix a distal projecting cannulated tube 304 (see FIG. 8) that houses a drive shaft 303 that is a component of length control mechanism 300.

Figure 8:
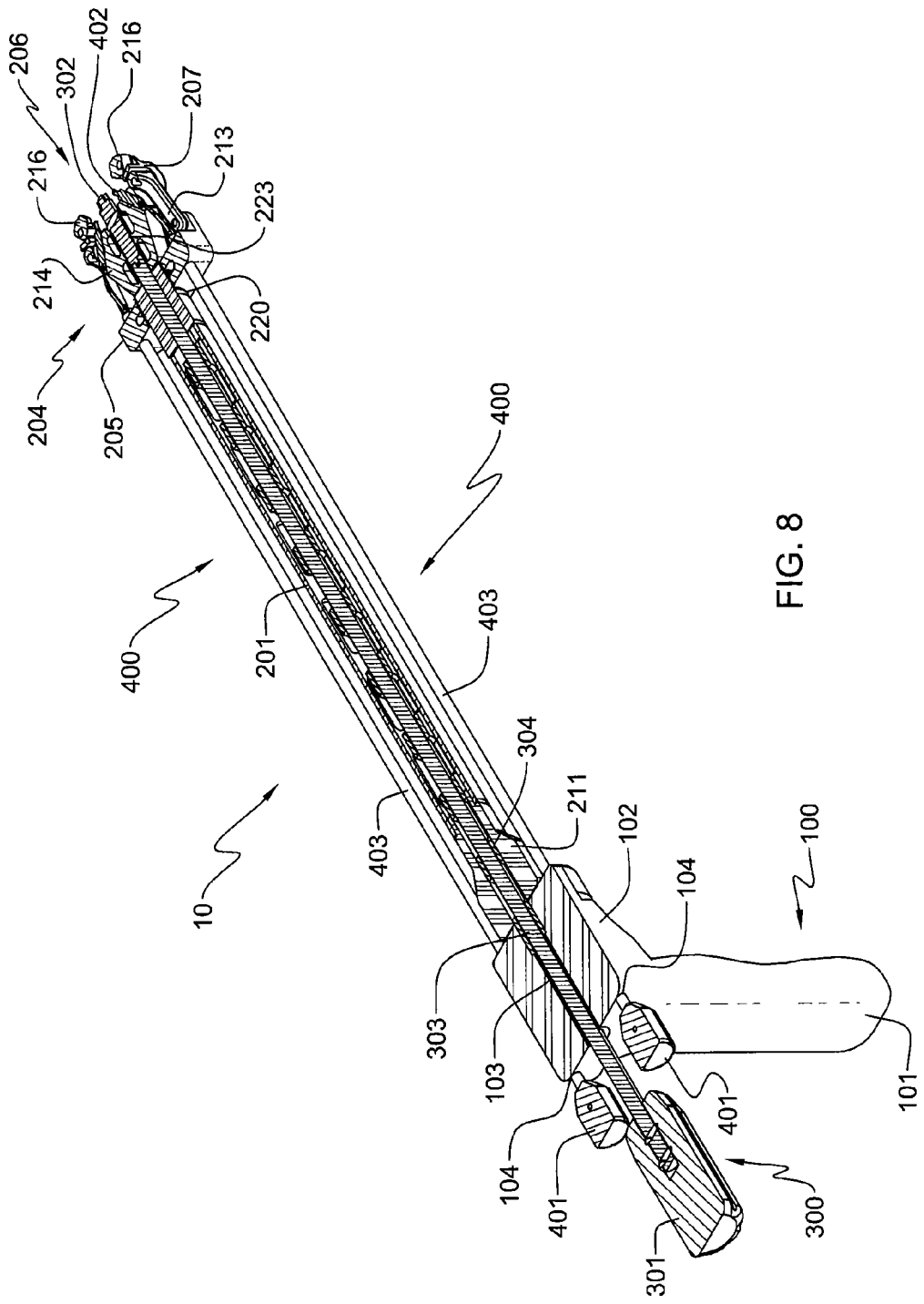
FIG. 8 a cross-sectional, perspective view of the surgical instrument of FIG. 1 taken along line 8-8, showing a top portion of the handle assembly, the elongate member and the implant engagement assembly, the length control mechanism and the locking mechanism, in accordance with an aspect of the present invention.

As seen in FIGS. 1 and 8, positioned on either side of hole 103 are two substantially parallel through holes 104 that are sized to receive the connecting rods 403 for the at last one locking mechanism 400. The embodiment shown for example purposes in FIG. 8, depicts two substantially parallel holes 104 that are sized to receive connecting rod 403 of locking mechanism 400. Holes 104 are configured to allow rotary motion of connecting rod 403 when an operating surgeon is using surgical instrument 10 to secure the overall length of an implant.

Positioned intermediate handle assembly 100 and actuation body 205 is elongate member 201. FIGS. 1, 3 and 4 show elongate body 201 extending in a proximal to distal direction with a first end 202 being located adjacent to handle assembly 100 and a second end 203 being moveably or rotatably connected to distally positioned implant engagement assembly 204 or more specifically, to actuation body 205. As seen in FIGS. 1, 2, 3 and 4, elongate member 201 is tube-like in structure with a round cross-sectional shape, although it is further contemplated that various geometric shaped cross-sections may be used in constructing elongate member 201, including, but not limited to oval, square, square, rectangular and other polygonal shapes. Further, as shown in FIG. 8, elongate member 201 is hollow with the inner diameter being sized to accommodate and surround cannulated tube 304. First end 202 is generally shaped as a gripping portion 211 with the configuration providing the operating surgeon with increased surface area and texture to grip and turn elongate member 201 when necessary. Second end 203 is typically configured to include a set of external threads 212 that will threadingly engage actuation body 205. When the operating surgeon rotates elongate member 201, the engaged actuation body 205 moves distally resulting in holding portion 206 engaging and grasping the implant. If the operating surgeon were to reverse the direction of rotation of elongate member 201, this would result in engaged actuation body 205 moving proximally relative to elongate member 201 and cause holding portion 206 to expand and release the implant from between first and second arms 207, 208.

Figure 2:
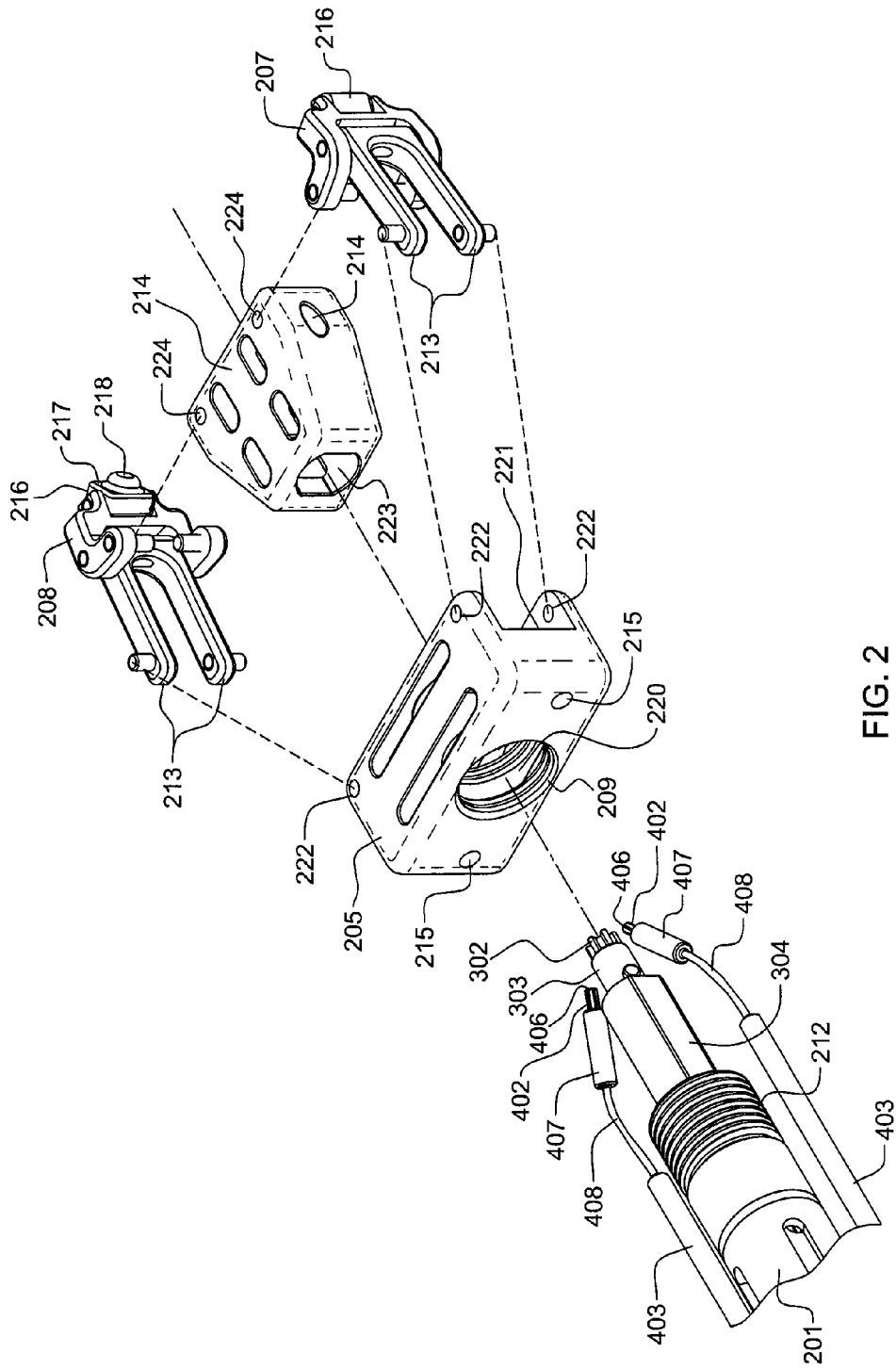
FIG. 2 is an enlarged, exploded perspective view of a distal end of the surgical instrument of FIG. 1 showing the distal aspects of an elongate member and a locking mechanism with an implant engagement assembly that includes an actuation body, a holding portion and an alignment body, in accordance with an aspect of the present invention.

FIG. 2 is an exploded view that shows implant engaging assembly 204 in more detail, specifically actuation body 205 and holding portion 206. Actuation body 205 may further be constructed to include a through central hole 220 with internal threads 209 that engage external threads 212. At least two through holes 215 are laterally positioned and may be sized to receive connecting rods 403. A slotted transverse opening 221 that is sized to slidingly engage the alignment body 214 is positioned in the distal aspect of actuation body 205. Connecting holes 222 for coupling the drive links 213 may also be constructed in the superior and inferior surfaces of the distal aspect of actuation body 205. A through hole 223 is positioned along the midline of alignment body 214 and it is sized to receive cannulated tube 304 and drive shaft 303. In addition, alignment body 214 may include fixation holes 224 that allow for the moveably coupling of arms 207, 208.

Figure 5:
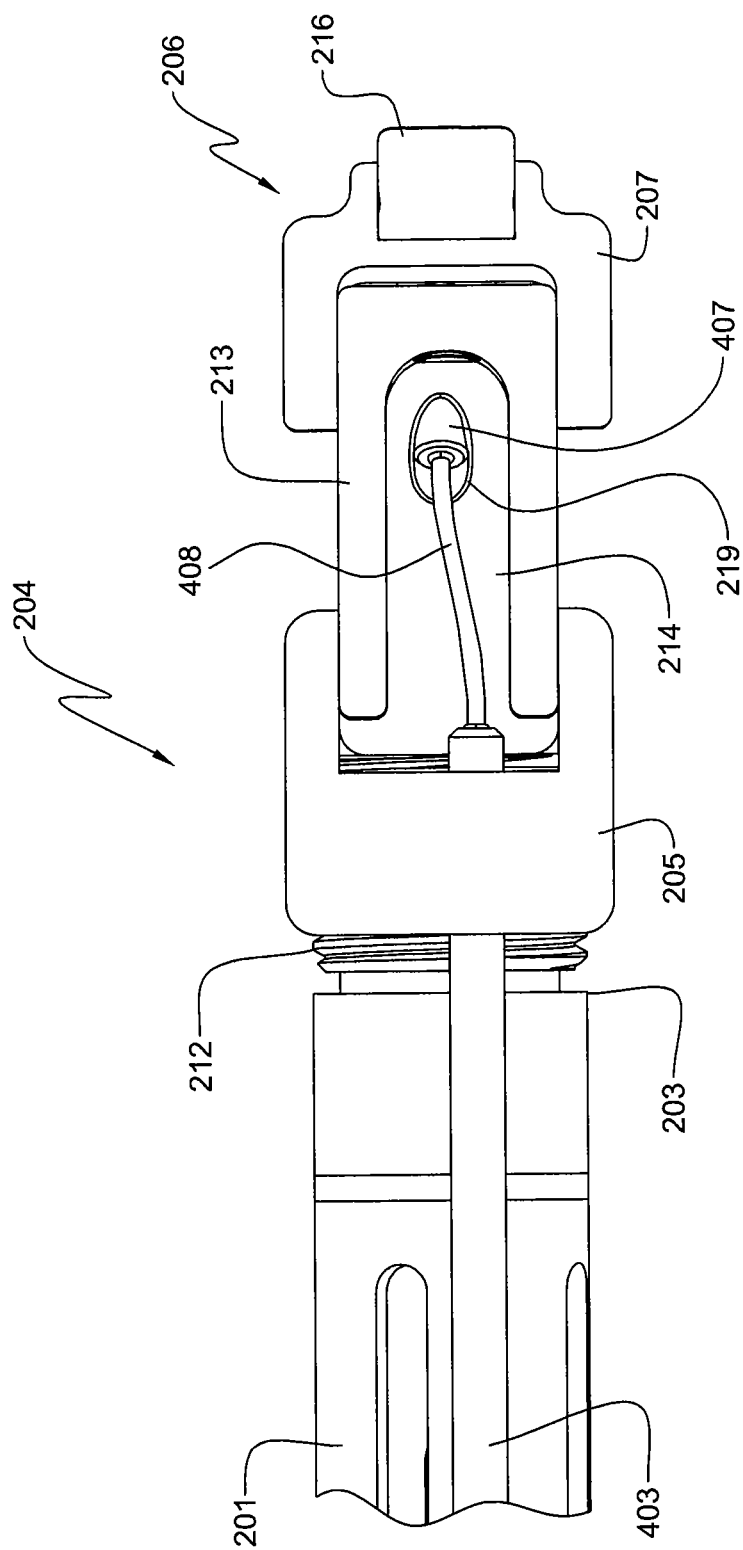
FIG. 5 is an enlarged, side elevational view of the assembled distal end of the surgical instrument of FIG. 1 showing the elongate member with external threads, the locking mechanism with a bearing portion, the implant engagement assembly, including the actuation body and holding portion with engagement member and the alignment body, in accordance with an aspect of the present invention.
Figure 6:
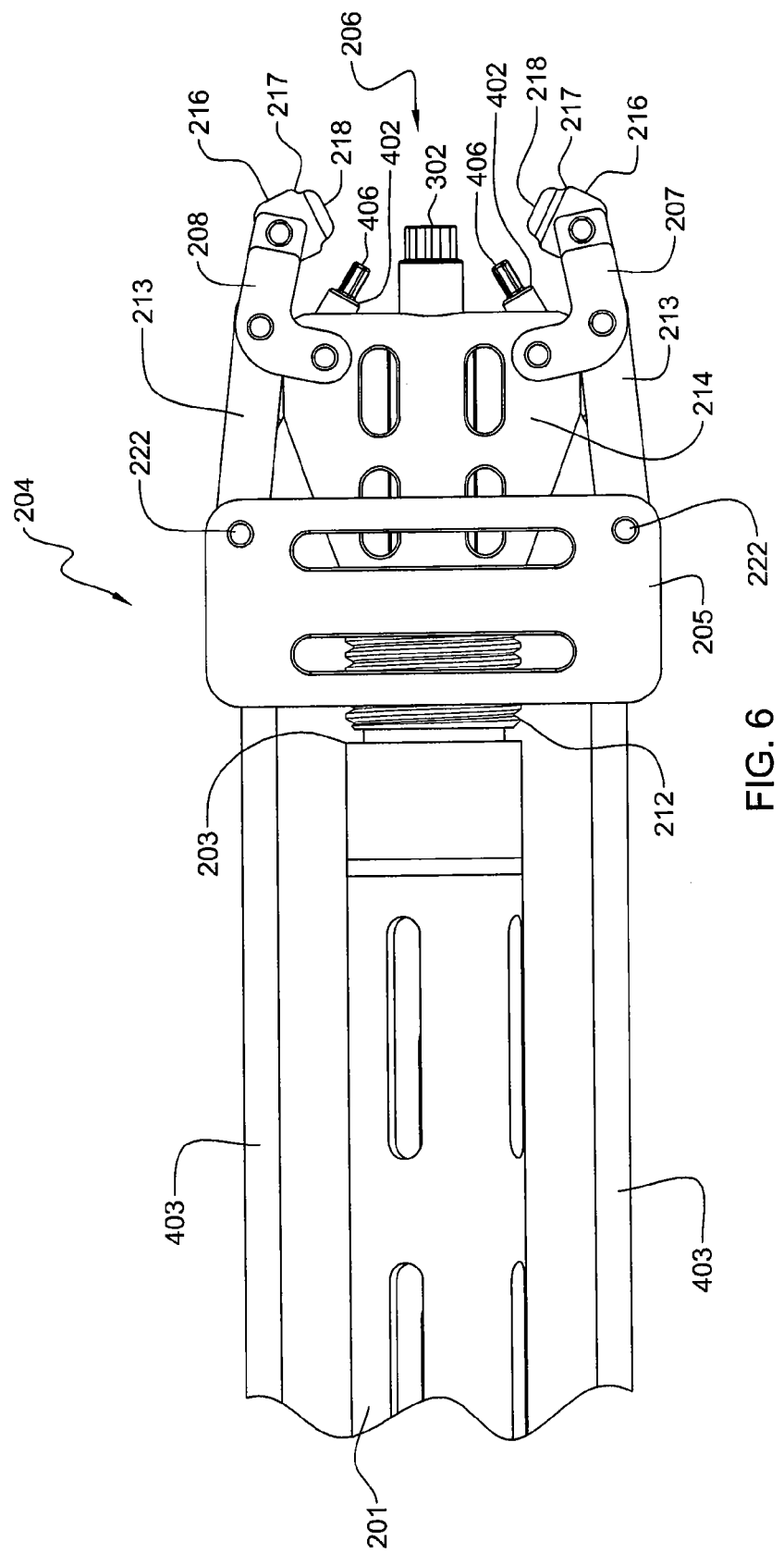
FIG. 6 is an enlarged, top view of the assembled distal end of the surgical instrument of FIG. 1 showing the elongate member with external threads, the locking mechanism with a coupling end, the implant engagement assembly, including the actuation body and the holding portion that includes the first and second arms and corresponding engagement members and the alignment body. Also seen, is the distal end of a length control mechanism, including a gear assembly, in accordance with an aspect of the present invention.
Figure 7:
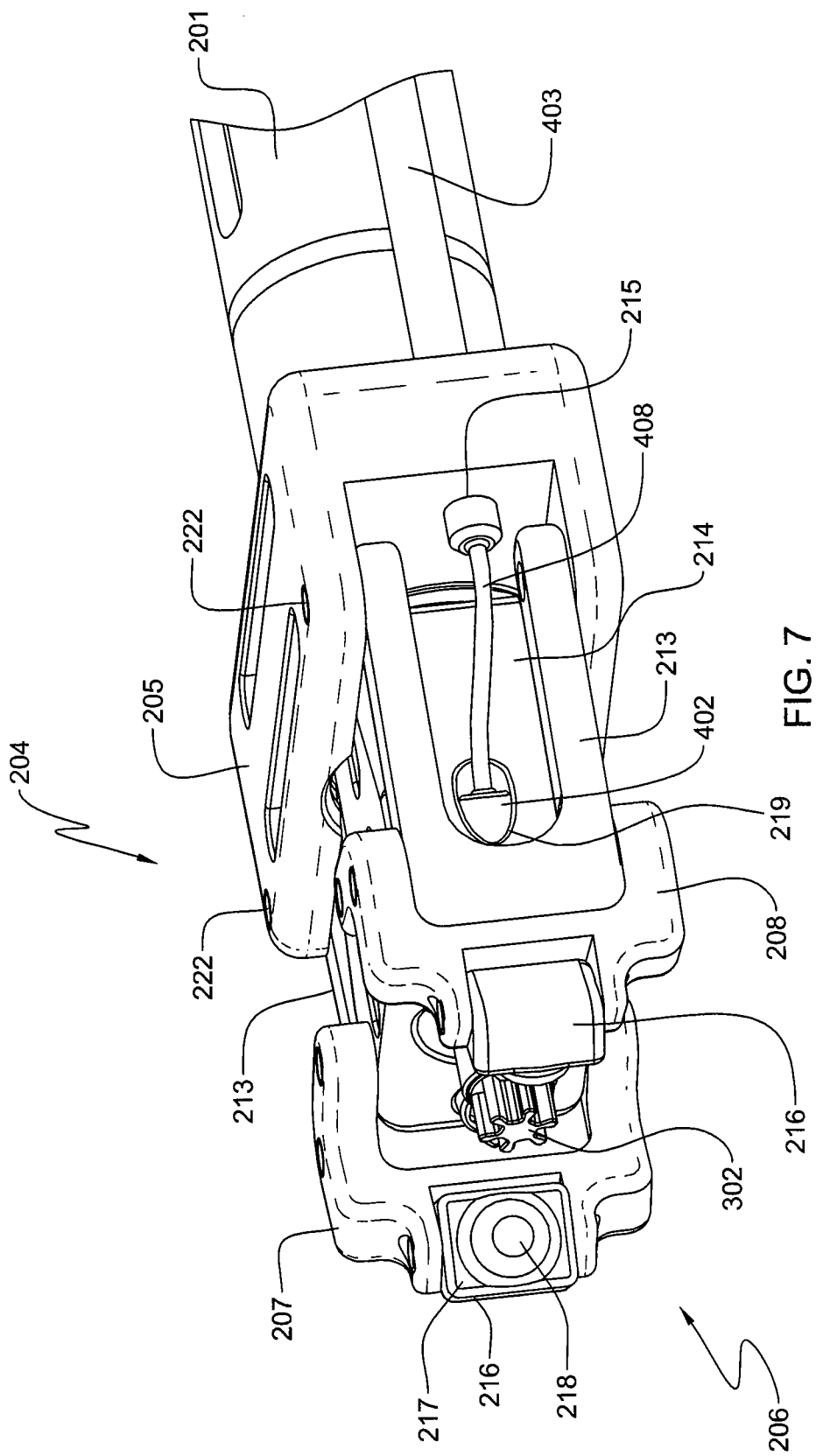
FIG. 7 is an enlarged, perspective view of the assembled distal end of the surgical instrument of FIG. 1 showing the elongate member, the locking mechanism with the bearing portion, the implant engagement assembly including the actuation body and the holding portion that includes the first and second arms with the corresponding engagement members and the alignment body. Also seen, is the distal end of the length control mechanism with the gear assembly, in accordance with an aspect of the present invention.

Holding portion 206 as seen in FIGS. 5, 6 and 7 generally includes alignment body 214, drive links 213, first arm 207 and second arm 208 with attached engagement members 216 positioned at the distal aspect of the first and second arms 207, 207. Holding portion 206 is constructed to allow for first and second arms 207, 208 to move in a direction towards the midline of surgical instrument 10 and then away from the midline when drive links 213 are moved either distally or proximally, respectively.

As seen in FIG. 6, drive links 213 are attached to actuation body 205, therefore as discussed above, when elongate member 201 is threaded into actuation body 205 and move actuation body 205 in either a distal or proximal direction, the distally attached drive links 213 will then cause first and second arms 207, 208 to move either towards the midline or away from the midline. First and second arms 207, 208 are generally configured as L-shaped bodies to facilitate continuous movement when coupled to drive links 213.

FIGS. 2 and 6 also depict the two engagement members 216 that are positioned at the distal ends of first and second arms 207, 208. Engagement members 216 are attached to the distal ends of first and second arms 207, 208 in a manner that allows engagement members 216 to pivot and rotate around the arm ends. This pivoting motion coupled with the movability of arms 207, 208 allows surgical instrument 10 to accommodate a broad range of sizes of implants including implants with variable widths or diameters. Engagement members 216 have a distal surface 217 that includes an attached engagement element 218 that is sized to engage or mate with a corresponding opening on the exterior surface of the implant.

As seen in FIGS. 2 and 6, for example purposes, engagement element 218 is configured as a knob-like structure, although it is contemplated that other protrusion-like structures including, but not limited to spring balls, rods or pins may be used.

FIGS. 1 and 4 further show length control mechanism 300 that functions to engage with the implant and mechanically change the overall length of the implant both through extension of the implant and contraction or shortening of the implant. This is generally accomplished by using the rotary motion of length control mechanism 300 that mates with a corresponding length adjustment mechanism in the implant. The length adjustment mechanism of the implant is designed to convert the rotary motion of the length control mechanism 300 to translational motion, wherein the overall linear length of the implant is then changed. Length control mechanism 300 includes a gripping portion 301 that is positioned at the proximal end of surgical instrument 10. Gripping portion 301 is typically shaped as a knob or other similar structure to allow the operating surgeon easy manipulation. Gripping portion 301 is connected to the proximal end of drive shaft 303 that extends generally in a proximal to distal direction and is also substantially parallel to longitudinal axis 210.

As seen in FIG. 8, drive shaft 303 passes through hole 103 and is encased by cannulated tube 304 within handle assembly 100. Cannulated tube 304 is sized to allow drive shaft 303 to move in a distal to proximal direction and rotate. Attached to the distal end of drive shaft 303 is a gear assembly 302.

FIGS. 2, 4 and 6 show gear assembly 302 extending to a distance that is generally between arms 207, 208 that enables gear assembly 302 to enter through one of the several holes of the implant to engage the length adjustment mechanism of the implant. As seen in FIG. 2, gear assembly 302 is secured to the distal end of drive shaft 303 approximately proximate to the exit point of drive shaft 303 from cannulated tube 304. Because of the securement of gear assembly 302 directly to drive shaft 303, when gripping portion 301 is rotated clockwise, this directional motion is directly translated to gear assembly 302 that correspondingly rotates in a clockwise direction. It should be noted that length control mechanism 300 may be rotated both in a clockwise and counter-clockwise direction depending on whether the surgeon is lengthening (expanding) or shortening (contracting) the implant.

FIGS. 1, 4 and 8 generally exhibit locking mechanism 400. For example purposes, surgical instrument 10 as depicted in these figures includes two locking mechanisms 400, although it is contemplated that only one locking mechanism may be necessary for securing the overall length of the implant post-implantation. As seen in the cross-section view of FIG. 8, locking mechanism 400 has a gripping portion 401 that is positioned near the proximal end of surgical instrument 10 and proximate to handle assembly 100. Gripping portion 401 is typically configured as a knob or other handle-like shape to allow the operating surgeon easy grasping and manipulation when in use. Connected to gripping portion 401 is connecting rod 403 that extends in a proximal to distal direction and substantially parallel to longitudinal axis 210. Connecting rod 401 passes through hole 104 in handle assembly 100, with hole 104 being sized to allow for rotational and translational movement of connecting rod 403 without any impingement. Connected to the distal portion of connecting rod 403 is coupling end 402. (See FIG. 2.)

As seen in FIGS. 2, 5 and 7, connecting rod 403 may include transition portion 408 that may be slightly curved and fabricated from a flexible material to allow for curving of coupling end 402 and entry into alignment body 214. Examples of possible flexible materials to use to construct transition portion 408 include nitinol or other elastic/psuedoelastic metals and various compliant polymers, including but not limited to polyethylene and polystyrene. Coupling end 402 further includes a distal tip 406 that is configured to allow for detachably coupling of the locking pin/screw following securement within the implant. As seen in FIG. 6, distal tip 406 may be shaped as a hex or other geometric shape that would in turn match up with the head of the corresponding locking pin/screw.

FIGS. 2, 5 and 6 show further that connecting rod 403 may also include a bearing portion 407 that slidingly engages with a slot 219 that is positioned in the lateral side of alignment body 214. Slot 219 is generally sized to allow for rotational and translational movement of bearing portion 407 while also correctly aligning tip 406 with a hole in the side of the implant for the insertion of the locking pin/screw. Depending on whether there are one or two locking mechanisms 400 present in the invention will determine the number of slots 219 present in alignment body 214. Although not shown, it would be understood by one skilled in the art that the locking pin/screw may include external threads for engaging the side hole of the implant or the internal length adjustment mechanism. An alternative locking mechanism either on the head or engagement end of the locking pin/screw may be used to secure the locking pin/screw to the internal length adjustment mechanism of the implant.

As shown in FIG. 4, surgical instrument 10 may use two locking mechanisms 400. If this is the case, connecting rods 403 will generally run parallel to each over the length of surgical instrument 10. Having two locking mechanisms 400 present allows the operating surgeon to secure the implant at two locations to ensure long term stability of the overall length of the implant post-operatively.

The surgical technique for implantation of an implant 700 is well known in the art, including the appropriate surgical exposure and dissection techniques. The method generally includes, obtaining an implant 700 and surgical instrument 10 that may include handle assembly 100 positioned at the proximal end of surgical instrument 10, elongate member 201 having a first end 202 being located adjacent to handle assembly 100 and second end 203 connected to implant engagement assembly 204. Surgical instrument 10 may further have length control mechanism 300, which generally will be constructed of gripping portion 301, gear assembly 302 and drive shaft 303. Surgical instrument 10 may yet further have at least one locking mechanism 400 that has gripping portion 401, coupling end 402 and connecting rod 403. It should be understood that all of the above noted instrument components and respective elements include the same structural and functionality characteristics as described previously herein.

The method may further include the step of coupling implant 700 to implant engagement assembly 204, or more specifically engagement member 216. Implant 700 is grasped or held by surgical instrument 10 when the operating surgeon places implant 700 between engagement members 216. The operating surgeon then rotates either clockwise or counterclockwise elongate member 201 via holding gripping portion 211 depending on whether arms 207, 208 need to be spread farther apart or brought closer together to make contact with implant 700. The operating surgeon may forego holding onto the gripping portion 211 and may also turn elongate member 201 along its shaft as well. Upon rotation of elongate member 201, external threads 212 engage internal threads 209 of actuation body 205 causing actuation body 205, depending on the direction of rotation of elongate member 201, to move either proximally or distally. Movement of actuation body 205 results in drive links 213 actuating arms 207, 208 to either move closer together to grasp the implant or farther apart to release the implant from between engagement members 216. The pivoting connection between arms 207, 208 and engagement member 216 allows holding portion 206 to accommodate and engage a wide range of sizes, configurations and diameters of implants.

Figure 9:
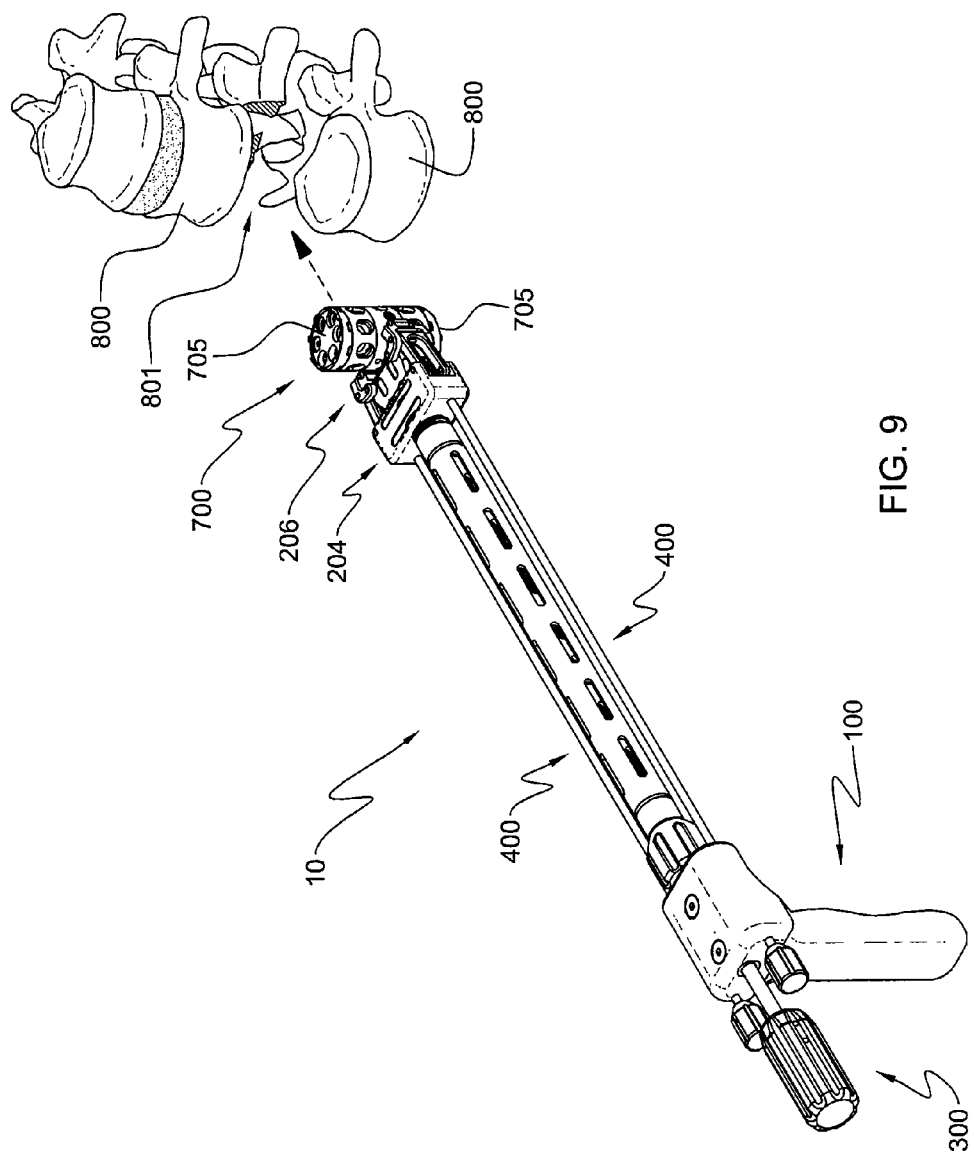
FIG. 9 is a perspective view of a spinal implant coupled to the surgical instrument of FIG. 1, shown positioned prior to insertion into a space between two vertebral bodies, in accordance with an aspect of the present invention.

As shown in FIG. 9, the surgical method may also include the steps of inserting surgical instrument 10 and the attached implant 700 through the skin opening and positioning the attached implant 700 adjacent to a space 801 between the two target bones 800. For example purposes only, as seen in FIG. 9, the two bones may be vertebral bodies or vertebrae 800.

FIGS. 10 and 11 exhibits a possible further step of the method, the extension or contraction of the overall length of implant 700 until the two ends 705 (Not Shown) of implant 700 make contact with vertebrae 800 resulting in a force being applied by implant 700 to maintain the space opening between the two vertebrae 800. The overall length of implant 700 may be extended or contracted (shortened) by rotating length control mechanism 300 either in a clockwise or counter-clockwise direction. Following the engagement of implant 700 with holding portion 206 of surgical instrument 10, the operating surgeon will push gripping portion 301 in a proximal direction resulting in drive shaft 303 and attached gear assembly 302 also moving proximally, with gear assembly 302 entering hole 702. Although not shown, gear assembly 302 will upon moving into the inner part of implant 700 engage a correspondingly configured length adjustment mechanism. Once gear assembly 302 is engaged with the length adjustment mechanism, the operating surgeon will turn gripping portion 301 either in a clockwise or counter-clockwise direction. When gripping portion 301 is rotated, drive shaft 303 and connected gear assembly 302 will also rotate. As described in the above-noted pending applications that have been incorporated herein by reference, length adjustment mechanism of implant is configured to convert the rotational movement of gear assembly 302 into translational movement within the implant. Essentially, when length control mechanism 300 is rotated in one direction implant 700 will extend or get longer and rotating length control mechanism 300 in the opposition direction will shorten or contract implant 700 while implant is placed between two bones. This novel functionality provides the operating surgeon with the ability to accurately adjust and ensure proper implant sizing without compromising positioning within the operative space.

FIGS. 11 and 12 show further the possible step of fixing or securing the overall length of implant 700 by the insertion of locking pins/screws 405 into holes 704 of implant 700 once the appropriate overall length has been determined. The operating surgeon uses locking mechanism 400 by initially coupling locking pins 405 to tips 406 (Not Shown). Following the final positioning and sizing of the implant in vivo, the operating surgeon will hold and turn gripping portion 401 that in turn rotates connecting rod 403. Depending on the locking or thread configuration of locking pin 405 and hole 704, gripping portion 401 may be turned either in a clockwise or counter-clockwise direction. Gripping portion 401 is then pushed in a proximal direction causing locking pin 405 to enter hole 704 and engage either threads or another securement configuration within implant 700. Following the rotational insertion of locking pin 405 into hole 704, the length adjustment mechanism will be locked in place, thereby fixing the overall length of implant 700. Once locking pin 405 is fully seated, the operating surgeon will move locking mechanism 400 in a distal direction and uncouple tip 406 from locking pin 405.

It should be understood by those skilled in the art that the surgical method and use of surgical instrument 10 described herein may be performed using either anterior, posterior or lateral approaches to the example spinal column. In addition, an operating surgeon may use a minimally invasive surgical approach and employ surgical instrument 10 because of the multi-functionality (i.e., grasp, extend/contract and lock) operation of surgical instrument 10 relative to implant 700. It is further contemplated that surgical instrument 10 may be sized to allow for endoscopic insertion. Having these multiple functions incorporated into one instrument addresses a long felt need of providing the operating surgeon with the ability to keep one instrument in the wound and to not have to repeatively remove the instrument and replace it with a different instrument to perform another function. Having a multi-purpose surgical instrument will lessen the potential for tissue disruption and adjacent structural damage.

It is further contemplated that a method of fabricating surgical instrument 10 may include the steps of providing handle assembly 100 with an additional step of providing elongate member 201 with one end 202 of the elongate member 201 being positioned adjacent to handle assembly 100 and second end 203 of elongate member 201 being moveably or threadingly connected to implant engagement assembly 204. Rotational movement of elongate member 201 relative to handle assembly 100 and implant engagement assembly results in the grasping and holding of the implant between engagement members 216.

The fabrication method may also include the further step of providing a length control mechanism 300 that typically allows the operating surgeon to adjust the overall length of the implant while holding the implant in place between engagement members 216. Yet a further step of the method may include providing at least one locking mechanism 400 for the surgical instrument 10. Locking mechanism 400 permits the operating surgeon with the ability to secure and fix the overall length of the implant after the final positioning and sizing is accomplished in vivo.

It is further contemplated that a spinal implant insertion kit comprised of various cross-sectional sizes, cross-sectional polygonal and circular/oval shapes and longitudinal lengths of implants and a corresponding surgical instrument 10 will be available as a kit. This will allow the operating surgeon to pick and choose these modular components that are necessary to assemble a spinal implant that best fits into a certain spinal segment or to address a certain anatomical deformity presented in a patient. The kit would further include a single inserter 10 that may be used with the multiple sized (both length and diameter) spinal implants. It is also contemplated that multiple sized inserters may be included in the kit to accommodate the various anatomic regions of the spine and the corresponding implant sizes (i.e., lumbar, thoracic and cervical). Inserter 10 includes handle assembly 100, elongate member 201, length control mechanism 300 and at least one locking mechanism 400. For brevity sake, all of the above noted inserter components and respective elements will not be discussed again here and include the same structural and functionality characteristics as described previously herein.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A surgical instrument for inserting an implant between two bones, the surgical instrument comprising:
   a handle assembly; and
   an elongate member having a first end and a second end, and a longitudinal axis extending there between, the elongate member being moveably connected to an implant engagement assembly, the implant engagement assembly being at a distal end of the surgical instrument and comprising a holding portion that includes first and second arms, a distal end of each of the first and second arms having an engagement member attached thereto, each engagement member being configured to pivot and rotate about the distal end of their corresponding arm and to hold the implant;
   wherein upon movement of the elongate member relative to the implant engagement assembly, the implant engagement assembly adjusts the implant for insertion between the two bones.

2. The surgical instrument of claim 1, wherein the implant engagement assembly further comprises an actuation body operatively coupled to the second end of the elongate member, wherein the first arm and the second arm of the holding portion is operatively coupled to the actuation body and configured to move and engage the implant upon actuation of the actuation body.

3. The surgical instrument of claim 2, wherein the engagement members are configured to operatively engage the implant upon activation of the actuation body.

4. The surgical instrument of claim 3, wherein each engagement member further comprises a distal surface, the distal surface having an engagement element disposed thereon, the engagement element being sized and configured to hold the implant in position after actuation of the actuation body.

5. The surgical instrument of claim 1, wherein the first end of the elongate member is configured as a gripping portion and the second end of the elongate member comprises external threads, the threads being sized and configured to threadingly engage the actuation body of the implant engagement assembly.

6. The surgical instrument of claim 1, wherein the elongate member is a cylindrical body.

7. The surgical instrument of claim 1, further comprising a length control mechanism for adjusting the overall length of the implant when the implant has been placed between the two bones.

8. The surgical instrument of claim 1, further comprising a locking mechanism for fixing the overall length the implant after the implant has been placed between the two bones.

9. The surgical instrument of claim 1, wherein the surgical instrument further comprises a first locking mechanism and a second locking mechanism, wherein the first locking mechanism and second locking mechanism are substantially parallel to each other and to the longitudinal axis of the elongate member.

10. A method of fabricating a surgical instrument for inserting an implant between two bones, the method comprising:
    providing a handle assembly; and
    providing an elongate member having a first end and a second end, and a longitudinal axis extending there between, the first end being positioned adjacent handle assembly and the second end being moveably connected to an implant engagement assembly, the implant engagement assembly being at a distal end of the surgical instrument and comprising a holding portion that includes first and second arms, a distal end of each of the first and second arms having an engagement member attached thereto, each engagement member being configured to pivot and rotate about the distal end of their corresponding arm and to hold the implant;
    wherein upon movement of the elongate member relative to the handle assembly and implant engagement assembly, the implant engagement assembly adjusts the implant for insertion between the two bones.

11. A surgical instrument for inserting an implant between two bones, the surgical instrument comprising:
    a handle assembly;
    an elongate member having a first end and a second end, and a longitudinal axis extending there between, the elongate member being moveably connected to an implant engagement assembly, the implant engagement assembly being at a distal end of the surgical instrument and being configured to hold the implant; and
    a first locking mechanism and a second locking mechanism, wherein the first locking mechanism and second locking mechanism are substantially parallel to each other and to the longitudinal axis of the elongate member;
    wherein upon movement of the elongate member relative to the implant engagement assembly, the implant engagement assembly adjusts the implant for insertion between the two bones,
    wherein the implant engagement assembly further comprises an actuation body and a holding portion, the actuation body being operatively coupled to the second end of the elongate member, and the holding portion comprising a first arm and a second arm, wherein the first arm and the second arm of the holding portion are operatively coupled to the actuation body and configured to move and engage the implant upon actuation of the actuation body, and
    wherein the first arm further comprises an engagement member and the second arm further comprises an engagement member, the engagement members being pivotally coupled to a distal end of the first arm and the second arm and are configured to operatively engage the implant upon activation of the actuation body.

12. The surgical instrument of claim 11, wherein the engagement member further comprises a distal surface, the distal surface having an engagement element disposed thereon, the engagement element being sized and configured to hold the implant in position after actuation of the actuation body.

13. The surgical instrument of claim 11, wherein the first end of the elongate member is configured as a gripping portion and the second end of the elongate member comprises external threads, the threads being sized and configured to threadingly engage the actuation body of the implant engagement assembly.

14. The surgical instrument of claim 11, wherein the elongate member is a cylindrical body.

15. The surgical instrument of claim 11, further comprising a length control mechanism for adjusting the overall length of the implant when the implant has been placed between the two bones.

16. The surgical instrument of claim 11, further comprising a locking mechanism for fixing the overall length the implant after the implant has been placed between the two bones.

* * * * *